United States Patent [19]
Underiner et al.

[11] Patent Number: 5,804,584
[45] Date of Patent: Sep. 8, 1998

[54] THERAPEUTIC COMPOUNDS CONTAINING A MONOCYCLIC FIVE- TO SIX-MEMBERED RING STRUCTURE HAVING ONE TO TWO NITROGEN ATOMS

[75] Inventors: Gail E. Underiner, Brier; David Porubek, Seattle; J. Peter Klein, Vashon Island; Paul Woodson, Edmonds, all of Wash.

[73] Assignee: Cell Therapeutics, Inc., Seattle, Wash.

[21] Appl. No.: 468,659

[22] Filed: Jun. 6, 1995

Related U.S. Application Data

[60] Division of Ser. No. 153,256, Nov. 16, 1993, abandoned, which is a continuation-in-part of Ser. No. 976,353, Nov. 16, 1992, Pat. No. 5,473,070.

[51] Int. Cl.⁶ .................... C07D 239/54; A61K 31/52
[52] U.S. Cl. .................... 514/269; 544/298; 544/242; 544/301; 544/302; 514/256
[58] Field of Search ..................... 514/242, 243, 514/269; 544/298, 299

[56] References Cited

U.S. PATENT DOCUMENTS

| | | | |
|---|---|---|---|
| 3,422,107 | 1/1969 | Mohler et al. | 544/271 |
| 3,737,433 | 6/1973 | Mohler et al. | 514/263 |
| 4,515,795 | 5/1985 | Hinze et al. | 544/267 |
| 4,576,947 | 3/1986 | Hinze et al. | 514/263 |
| 4,599,414 | 7/1986 | Sugimoto et al. | 544/269 |
| 4,612,315 | 9/1986 | Jacobson et al. | 544/269 |
| 4,636,507 | 1/1987 | Kreutzer et al. | 514/263 |
| 4,833,146 | 5/1989 | Gebert et al. | 514/263 |
| 4,845,102 | 7/1989 | Sakurai et al. | 514/263 |
| 4,965,271 | 10/1990 | Mandell et al. | 514/263 |
| 5,039,666 | 8/1991 | Novick et al. | 514/37 |
| 5,068,236 | 11/1991 | Suzuki et al. | 514/263 |
| 5,096,906 | 3/1992 | Mandell et al. | 514/263 |
| 5,118,500 | 6/1992 | Hänel et al. | 424/85 |

OTHER PUBLICATIONS

Bianco et al., *Blood*, 76:Supplement 1 (522), p. 133a, "Pentoxifylline (PTX) abd GM–CSF Decrease Tumor Necrosis Factor–Alpha (TNF–α) Levels in Patients Undergoing Allogenic Bone Marrow Transplantation (BMT)," 1991.

Bianco et al., *Blood*, 78:1205, "Phase I–II Trial of Pentoxifylline for Prevention of Transplant–Related Toxicities Following Bone Marrow Transplantation," 1991.

Davis et al., *Applied Environment Microbiol.*, 48:2, pp. 327–331, "Microbial Models of Mammalian Metabolism: Microbial Reduction and Oxidation of Pentoxifylline," Aug. 1984.

Kanehira et al. *Chem. Abst.*, 110:212848x, "Heterocyclic Amino Alcohols as Brain Function Improvers and Allergy Inhibitors," 1989.

Singer et al., *Bone Marrow Transplantation*, 10:19, pp. 19–25, "Effect of Methylxantine Derivatives on T Cell Activitation," 1992.

*Primary Examiner*—John M. Ford
*Assistant Examiner*—Pavanaram K. Sripada
*Attorney, Agent, or Firm*—McDermott Will & Emery

[57] ABSTRACT

Disclosed are therapeutic compounds having the formula:

(R)j–(core moiety), including resolved enantiomers, diastereomers, hydrates, salts, solvates and mixtures thereof. j is an integer from one to three, the core moiety is either non-cyclic or comprises at least one five- to seven-membered ring structure, R may be selected from the group consisting of hydrogen, halogen, hydroxyl, amino, substituted or unsubstituted benzyl, $C_{1-6}$ alkyl or $C_{1-6}$ alkenyl, and at least one R has the formula I:

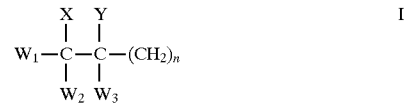

n is an integer from seven to twenty and at least one of X or Y is —OH. The other of X or Y, which is not —OH, is hydrogen, $CH_3$—, $CH_3$—$CH_2$—, $CH_3$—$(CH_2)_2$— or $(CH_3)_2$—$CH_2$—, and each $W_1$, $W_2$, and $W_3$ is independently hydrogen, $CH_3$—, $CH_3$—$CH_2$—, $CH_3$—$(CH_2)_2$— or $(CH_3)_2$—$CH_2$—. The X, Y, $W_1$, $W_2$, or $W_3$ alkyl groups may be unsubstituted or substituted by an hydroxyl, halo or dimethylamino group. The disclosed compounds and therapeutic compositions thereof are useful in treating individuals having a disease or treatment-induced toxicity, mediated by second messenger activity.

9 Claims, 10 Drawing Sheets

THERAPEUTIC COMPOUNDS CONTAINING A MONOCYCLIC FIVE- TO SIX-MEMBERED RING STRUCTURE HAVING ONE TO TWO NITROGEN ATOMS

CROSS REFERENCE TO RELATED APPLICATION

This is a Divisional of U.S. patent application Ser. No. 07/153,256, filed Nov. 16, 1993 now abandoned, which in turn is a Continuation-In-Part of U.S. patent application Ser. No. 07/976,353, filed Nov. 16, 1992 now patented U.S. Pat. No. 5,473,070.

TECHNICAL FIELD OF THE INVENTION

The invention provides a class of substituted hydroxyl-containing compounds that are effective agents to inhibit specific intra-cellular signaling events often induced by noxious or inflammatory stimuli, or to directly or indirectly be anti-microbial to yeast or fungal infections. More specifically, the inventive compounds have at least one hyroxyl-containing substituent bonded to core moiety. The inventive compounds are useful antagonists to control intra-cellular levels of specific non-arachidonyl sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX and disclosed in U.S. Pat. Nos. 3,422,307 and 3,737,433, is a xanthine derivative which has seen widespread medical use for the increase of blood flow. Metabolites of PTX were summarized in Davis et al., *Applied Environment Microbial.* 48:327, 1984. One such metabolite, 1-(5-hydroxyhexyl)-3,7-dimethylxanthine, designated M1 and disclosed in U.S. Pat. Nos. 4,515,795 and 4,576,947, increases cerebral blood flow. In addition, U.S. Pat. Nos. 4,833,146 and 5,039,666 disclose use of tertiary alcohol analogs of xanthine for enhancing cerebral blood flow.

U.S. Pat. No. 4,636,507 discloses that PTX and M1 stimulate chemotaxis in polymorphonuclear leukocytes in response to a chemotaxis stimulator. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in bone marrow transplant-related complications accompanied reduction in assayable levels of TNF. However, in normal volunteers, TNF levels were higher among PTX recipients. Therefore, elevated levels of TNF are not the primary cause of such complications.

Therefore, effective therapeutic compounds that are safe and effective for human or animal administration and that can maintain cellular homeostasis in the face of a variety of inflammatory stimuli are needed. The invention is a result of research conducted in looking for such compounds.

SUMMARY OF THE INVENTION

We have found a genus of compounds useful in a large variety of therapeutic indications for treating or preventing disease mediated by intracellular signaling through one or two specific intracellular signaling pathways. In addition, the inventive compounds and pharmaceutical compositions are suitable for normal routes of therapeutic administration (e.g., parenteral, oral, topical, etc.) for providing effective dosages.

The invention provides a class of compounds containing at least one hydroxyl-containing side chain of at least nine carbon atoms in length, preferably cyclic compounds. The inventive compounds and pharmaceutical compositions thereof have the formula:

$(R)j$–(core moiety), including resolved enantiomers and/or diastereomers, hydrates, salts, solvates and mixtures thereof, wherein j is an integer from one to three, the core moiety is either non-cyclic or comprises at least one five- to seven-membered ring structure, and R may be selected from the group consisting of hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom. Preferred R include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or H, and most preferably, methyl or H. At least one R has the formula I:

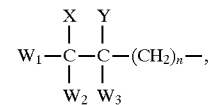  I wherein n is an integer from seven to twenty and at least one of X or Y is —OH. If only one of X or Y is —OH, then the other X or Y is hydrogen, $CH_3$—, $CH_3$—$CH_2$—, $CH_3$—$(CH_2)_2$—, or $(CH_3)_2$—$CH_2$—, and $W_1$, $W_2$, and $W_3$ are independently hydrogen, $CH_3$—, $CH_3$—$CH_2$—, $CH_3$—$(CH_2)_2$—, or $(CH_3)_2$—$CH_2$—, wherein X, Y, $W_1$, $W_2$, and $W_3$ alkyl groups may be substituted by an hydroxyl, halo or dimethylamino group and/or interrupted by an oxygen atom, hydrogen or alkyl ($C_{1-4}$). Preferably, n is an integer from seven to twelve. Especially preferred compounds have X and Y both being —OH and each of $W_1$, $W_2$, and $W_3$ being hydrogen or methyl.

A non-cyclic core moiety may be, for example, an amino acid (one or two), an hydroxyl, carboxyl, sulfoxide, sulfonate, phosphate, amide, amine, or ketone group, a simple ionic functional group, or a terminal hydrogen or halogen atom. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may alternatively be at least one five- to seven-membered ring, preferably having from one to three, five- to six-membered ring structures in a predominantly planar configuration. Preferably, R having formula I structure is bonded to a ring nitrogen if one exists. Exemplary, cyclic-core moieties may be substituted or unsubstituted:

barbituric acid; benzamide; benzene; biphenyl; cyclohexane, cyclohexene; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil; xanthine; or derivatives thereof.

Preferred ring cores include substituted or unsubstituted glutarimide, methylthymine, methyluracil, thymine, theobromine, uracil and xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2-hydroxypyridine; methyldihydroxypyrazolopyrimidine (preferably, 1,3-dimethyldihydroxypyrazolo[4,3-d] pyrimidine); methylpyrrolopyrimidine (preferably, 1-methylpyrrolo [2,3-d] pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4 (3H)-one; alkyl-substituted ($C_1$ -6) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, the ring-core is xanthine or a xanthine derivative. Especially preferred xanthine compounds have the following formula II:

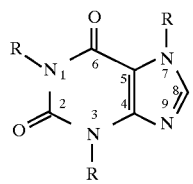

wherein R is selected from the foregoing members. Most preferably, a single R having formula I above is bonded to the $N_1$ xanthine nitrogen in formula II or each of two formula IR are bonded to $N_1$ and $N_7$ xanthine nitrogens, respectively. Remaining R substituents are preferably selected from the group consisting of hydrogen, methyl, fluoro, chloro and amino.

The invention provides a pharmaceutical composition comprising an inventive compound and a pharmaceutically acceptable excipient. The pharmaceutical composition may be formulated for oral, parenteral, ocular or topical administration to a patient.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger described herein. The second messenger pathway is activated in response to various noxious, proinflammatory or proliferative stimuli characteristic of a variety of disease states. More specifically, the invention includes methods for treating or preventing clinical symptoms of various disease states or reducing toxicity of other treatments by inhibiting cellular signaling through a second messenger pathway involving signaling through a non-arachidonyl phosphatidic acid intermediate.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by proinflammatory cytokines including tumor necrosis factor (TNF) and IL-1, and rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesengial cell proliferation in response to IL-1, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation in response to inflammatory stimuli (e.g., TNF, IL-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases resulting from over-stimulation by proinflammatory neurotransmitters such as, acetylcholine, serotonin, leuenkephalin or glutamate; acute inflammatory diseases such as septic shock, adult respiratory distress syndrome; multi-organ dysfunction associated with inflammatory cytokine cascade; and combinations thereof.

In many cell types, signaling is dependent upon generation of a broad variety of non-arachidonyl PA species, some of which are generated from lyso-PA by the enzyme lyso-PA acyl transferase (LPAAT). Generation of each of these PA species (the predominant forms being: 1-acyl and 1-alkyl 2-linoleoyl PA compounds, generated by LPAAT) serves to effect both proliferative and/or inflammatory signaling in the diseases discussed and cell systems described above.

The inventive compounds are of particular significance for inhibiting IL-2-induced proliferative response. IL-2 signaling inhibition is potentially useful in the treatment of numerous disease states involving T-cell activation and hyperproliferation. Exemplary autoimmune diseases are lupus, scleroderma, rheumatoid arthritis, multiple sclerosis, glomerula nephritis, insulin dependent diabetes mellitus (IDDM), as well as potential malignancies, including but not limited to, chronic myelogenous leukemia as well as others.

DETAILED DESCRIPTION OF THE INVENTION

Figure 1:
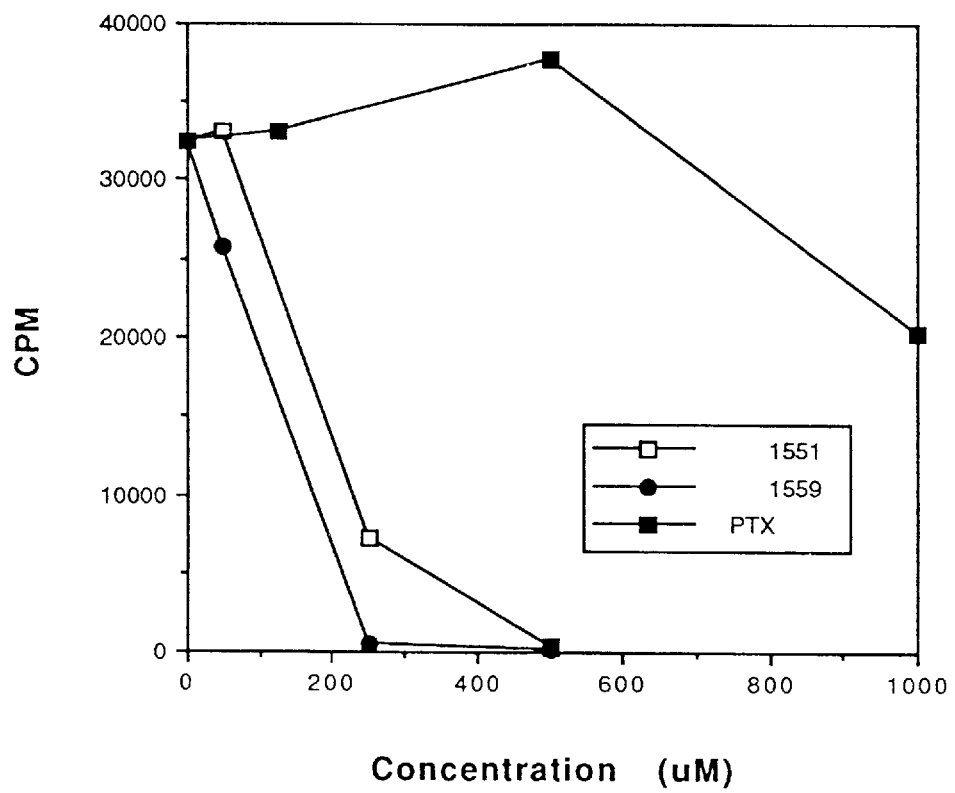
FIG. 1 shows a mixed lymphocyte reaction of PTX and two inventive compound nos. 1551 and 1559 (chemical names and structures below). The mixed lymphocyte reaction shows a proliferative response of PBMC (peripheral blood mononuclear cells) to allogeneic stimulation determined in a two-way mixed lymphocyte reaction. Each of the inventive compounds tested was more effective and more potent than PTX in this immune modulating activity assay procedure.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are preferably, substantially enantiomerically pure, and preferably are the R enantiomer at the chiral carbon atom bonded to the hydroxyl group.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific-second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications, mediated at the cellular level by a common mechanism of action. Moreover, in vitro and in vivo data, presented herein, provides predictive data that a wide variety of clinical indications, having similar effects on the specific second messenger pathway, may be treated by the inventive compounds, which specifically inhibit the pathway, activated by noxious stimuli and mediated through, for example, inflammatory cytokines. In fact, the mechanism of action for the inventive compounds explains why these compounds have a multifarious clinical indications.

Activation of the second messenger pathway is a major mediator of response to noxious stimuli and results in cellular signals that lead to, for example, acute and chronic inflammation, immune response and cancer cell growth. Although the inventive compounds may desirably inhibit many other unmentioned, noxious stimuli, they most effectively mediate the above conditions. Signals mediated by the present second messenger pathway include, for example, those cellular responses of LPS directly, T cell activation by antigen, B cell activation by antigen, cellular responses to IL-1 mediated through the IL-1 Type 1 receptor (but not the IL-1 Type 2 receptor), the TNF Type 1 receptor, growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL-4, IL-6 and IL-7 on T and B cells.

The foregoing in vitro effects give rise to the following in vivo biologic effects, including, but not limited to, protection and treatment of endotoxic shock and sepsis induced by gram positive or gram negative bacteria, inhibition of tumor cell growth, synergistic immunosuppression, active in autoimmune diseases and in suppressing allograft reactions, and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello and Wolff *N. Engl. J. Med.* 328, 106, Jan. 14, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension. The therapeutic advantage of blocking the action of IL-1 resides in preventing its deleterious biologic effects without interfering with the production of molecules that have a role in homeostasis. The present inventive compounds address the need, identified by Dinarello and Wolff, by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and i-o-alkyl or 1-o-alkenyl acylglycerol (AAG) species. The inventive compounds exert their activity by inhibiting one or both enzymes at the inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is about <0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG on stimulation with mitogens, although the sources of DAG have differed between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. The specific species of DAG that is stimulated by serum is dioleoyl and for PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic changes induced by PA/DAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* 330:662, 1987 and Hinshaw et al., *Circ. Shock* 30:279, 1990); cachexia (Dezube et al., *Lancet* 355:662, 1990), and adult respiratory distress syndrome (Miller et al., Lancet 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et al., *Nature* 344:245, 1990, and Bissonnette et al., *Inflammation* 13:329, 1989), and reperfusion injury (Vedder et al., *Proc. Natl. Acad. Sci. USA* 87:2643, 1990).

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al. (*Science* 253:1129, 1991) have shown that neointimal smooth muscle chemotaxis and angioplasty are inhibited in rats using a neutralizing antibody to PDGF. Also, Jawien et al. (*J. Clin Invest.* 89:507, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et al., *Cancer Res.* 52:5024, 1992), and glial tumors (Fleming et al., *Cancer Res.* 52:4550, 1992).

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

In Vitro Assays for Physiologic and Pharmacological Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 μl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 μCi/well of 40 to 60 Ci/mmole) and proliferation determined by liquid scintillation counting.

Another assay for measuring activity of the inventive compounds involves determining PDGF, FGF or VEGF proliferative response using either mouse NIH-3T3 (Balb) cells or human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 μg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Compounds of the Invention

The inventive compounds contain at least one hydroxyl-containing side chain of at least nine carbon atoms in length and are preferably cyclic compounds. The inventive compounds and pharmaceutical compositions thereof have the formula:

(R)j–(core moiety), including resolved enantiomers and/or diastereomers, hydrates, salts, solvates and mixtures thereof, wherein j is an integer from one to three, the core moiety is either non-cyclic or comprises at least one five- to seven-membered ring structure, and R may be selected from the group consisting of hydrogen, halogen (preferably bromine, chlorine, fluorine and iodine), hydroxyl, amino, substituted or unsubstituted benzyl, alkyl ($C_{1-6}$, preferably methyl) or alkenyl ($C_{1-6}$), preferably the alkyl or alkenyl groups being substituted by an hydroxy, halogen and dimethylamine and/or interrupted by an oxygen atom. Preferred R include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or H, and most preferably, methyl or H. At least one R has the formula I:

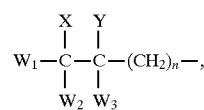

wherein n is an integer from seven to twenty and at least one of X or Y is —OH. If only one of X or Y is —OH, then the other X or Y is hydrogen, $CH_3$—, $CH_3$—$CH_2$—, $CH_3$—$(CH_2)_2$—, or $(CH_3)_2$—$CH_2$—, and $W_1$, $W_2$, and $W_3$ are independently hydrogen, $CH_3$—, $CH_3$—$CH_2$—, $CH_3$—$(CH_2)_2$—, or $(CH_3)_2$—$CH_2$—, wherein X, Y, $W_1$, $W_2$, and $W_3$ alkyl groups may be substituted by an hydroxyl, halo or dimethylamino group and/or interrupted by an oxygen atom, hydrogen or alkyl ($C_{1-4}$). Preferably, n is an integer from seven to twelve. Especially preferred compounds have X and Y both being —OH and each of $W_1$, $W_2$, and $W_3$ being hydrogen or methyl.

A non-cyclic core moiety may be, for example, an amino acid (one or two), an hydroxyl, carboxyl, sulfoxide, sulfonate, phosphate, amide, amine, or ketone group, a simple ionic functional group, or a terminal hydrogen or halogen atom. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be a dipeptide comprising two amino acids selected from the foregoing exemplary list. Exemplary core halogen atoms include bromine, chlorine, fluorine and iodine.

A core moiety may alternatively be at least one five- to seven-membered ring, preferably having from one to three, five- to six-membered ring structures in a predominantly planar configuration. Preferably, R having formula I structure is bonded to a ring nitrogen if one exists. Exemplary, cyclic-core moieties may be substituted or unsubstituted: barbituric acid; benzamide; benzene; biphenyl; cyclohexane, cyclohexene; cyclohexanedione; cyclopentanedione; delta-lactam; flutarimide; glutarimide; homophthalimide; imidazole amide; isocarbostyrile; lumazine; napthlalene; pteridine; pthalimide; piperidine; pyridine; pyrimidine; pyrrole amide; quinazolinedione; quinazolinone; quinolone; recorsinol; stilbene; succinimide; theobromine; thymine; triazine; tricyclododecane; uracil; xanthine; or derivatives thereof.

Preferred ring cores include substituted or unsubstituted glutarimide, methylthymine, methyluracil, thymine, theobromine, uracil and xanthine. Exemplary preferred cores include, but are not limited to: 1,3-cyclohexanedione, 1,3-cyclopentanedione; 1,3-dihydroxynaphthalene; 1-methyllumazine; methylbarbituric acid; 3,3-dimethylflutarimide; 2-hydroxypyridine; methyldihydroxypyrazolopyrimidine (preferably, 1,3-dimethyldihydroxypyrazolo[4,3-d] pyrimidine); methylpyrrolopyrimidine (preferably, 1-methylpyrrolo [2,3-d] pyrimidine); 2-pyrrole amides; 3-pyrrole amides; 1,2,3,4-tetrahydroisoquinolone; 1-methyl-2,4(1H,3H)-quinazolinedione (1-methylbenzoyleneurea); quinazolin-4 (3H)-one; alkyl-substituted ($C_{1-6}$) thymine; methylthymine; alkyl-substituted ($C_{1-6}$) uracil; 6-aminouracil; 1-methyl-5,6-dihydrouracil; 1-methyluracil; 5- and/or 6-position substituted uracils; 1,7-dimethylxanthine, 3,7-dimethylxanthine; 3-methylxanthine; 3-methyl-7-methylpivaloylxanthine; 8-amino-3-methylxanthine; and 7-methylhypoxanthine.

Preferably, the ring-core is xanthine or a xanthine derivative. Especially preferred xanthine compounds have the following formula II:

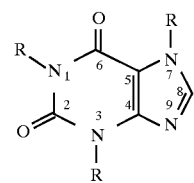

wherein R is selected from the foregoing members. Preferably, a single R having formula I above is bonded to the $N_1$ xanthine nitrogen in formula II or each of two formula I R are bonded to $N_1$ and $N_7$ xanthine nitrogens, respectively. Remaining R substituents are preferably selected from the group consisting of hydrogen, methyl, fluoro, chloro and amino.

Synthesis of the Inventive Compounds

The invention includes a method for preparing compounds according to the invention. Exemplary methods for preparing the inventive compounds are discussed below and in the following examples.

In a method according to the invention, a compound containing a desired core (intended as a "core moiety" in compounds of the invention) undergoes a reaction to produce an anion. The anion is then subsequently reacted with a substituted olefin to displace a targeted functional group on the olefin, resulting in an intermediate product. In a preliminary reaction, a predetermined amount of a core-containing compound is reacted with a suitable base, a solvent and a substituted olefin, the substituted olefin having at least one functional group which may be substituted in a displacement reaction by the desired core-containing compound.

Preferred bases include, but are not limited to, sodium hydride, sodium amide, sodium alkoxide, lithium hydride, potassium hydride, lithium amide, sodium amide and potassium amide. An especially preferred base is is sodium hydride. Preferred solvents may be dimethylsulfoxide, dimethylformamide, or an alcohol. Exemplary preferred alcohols include, but are not limited to, methanol, ethanol or isopropanol. Any substituted olefin comprising a chain structure of the inventive compounds may be used in the preliminary reaction according to the invention. Preferred olefins may be ω-substituted olefins. Preferred substituted olefins include, but are not limited to halo-substituted olefins.

The intermediate product, having a composite structure of the core-containing compound and substituted olefin may subsequently be converted to a corresponding compound having an hydroxyl functional group. Primary and other, less-substituted compounds are within the scope of the inventive compounds and methods. The intermediate product is reacted with a hydroborating agent to obtain a desired borane derivative. The borane derivative is subsequently reacted in an oxidative hydrolysis reaction with an oxidative-hydrolyzing agent to obtain the corresponding compound having the desired hydroxyl functional group. Exemplary hydroborating agents include, but are not limited to, diborane, borane-methyl sulfide complex, borane-pyridine complex, thexylborane, disiamylborane, and 9-borabicyclo[3.3.1]nonane, most preferably, borane-tetrahydrofuran complex. Exemplary oxidative-hydrolyzing agents include strong oxidizers such as a hydrogen peroxide solution and the like.

Alternatively, the inventive compounds may be prepared by reacting a compound having at least one hydroxyl group with a predetermined amount of a compound containing a desired core (intended as a "core moiety" in compounds of the invention) with a suitable base and a solvent. The compound having at least one hydroxyl group has at least one other functional group which may be substituted in a displacement reaction by the core-containing compound. Other functional group may be, for example, halogen atoms.

In another process for preparing the inventive compounds, the intermediate product, which may be prepared in the above-discussed procedure, may be converted to a corresponding diol by reacting the intermediate product with a suitable oxidizing agent. Preferred oxidizing agents include, but are not limited to, osmium tetroxide. Preferred oxidizing agents, such as osmium tetroxide may require a catalytic amount of the oxidizing agent in the presence of a regenerating agent. Exemplary, regenerating agents may be 4-methylmorpholine-N-oxide and trimethylamine-N-oxide. An especially preferred regenerating agent is 4-methylmorpholine-N-oxide.

The inventive method is also directed to a process for subsequently converting the intermediate product, having a composite structure-of the core-containing compound and substituted olefin, to a corresponding epoxide. In the method according to the invention, the intermediate product may be reacted with an organic peracid to obtain a desired epoxide. Preferred exemplary organic peracids include 3-chloroperoxybenzoic acid, peracetic acid and trifluoroperacetic acid. An especially preferred peracid is 3-chloroperoxybenzoic acid.

Subsequently, the corresponding epoxide is reacted with a reducing agent to convert the correponding epoxide to an inventive compound. Exemplary reducing agents may be selected from the non-exhaustive group of hydride reducing agent (preferably sodium borohydride or lithium aluminum hydride) or hydrogenating agent (such as, for example, hydrogen gas in the presence of a metal catalyst). Preferred metal catalysts may be, for example, palladium, platinum, or Raney nickel.

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diastereomers, is at least about 85% of a relevant optical isomer, preferably at least about 95% relevant optical isomer and especially at least about 99% or higher relevant optical isomer. Most preferably an amount of other optical forms is undetectable.

Chain length appears to exhibit some significance in predicting degree of activity of the compounds. For example, when n is 2 or less, the compounds show little activity in exemplary assays used herein. When n is 3 or 4, more activity is observed, particularly inhibitive activity in proliferation assays described herein. When n is 6 there is moderate activity. Activity increases significantly (on a potency basis) when n is 7 or greater. A steep-rising curve is apparent for compounds having n equal to 7, 8 or more.

The invention provides a pharmaceutical composition comprising an inventive compound and a pharmaceutically acceptable excipient. The pharmaceutical composition may be formulated for oral, parenteral or topical administration to a patient.

The invention further provides a pharmaceutical composition comprising an inventive compound and a pharmaceutically acceptable excipient, the pharmaceutical composition being formulated for oral, parenteral or topical administration to a patient. A pharmaceutical composition may alternatively comprise one or a plurality of inventive compounds and a pharmaceutically acceptable carrier or excipient. Treatment of individuals with an inventive compound or pharmaceutical composition may include contacting with the inventive compound in vitro culture, in an extracorporeal treatment, or by administering (oral, parenteral or topical) the inventive compound or pharmaceutical composition to a subject whose cells are to be treated.

Exemplary, preferred compounds of the invention include both R and S enantiomers and racemic mixtures of the following compounds:

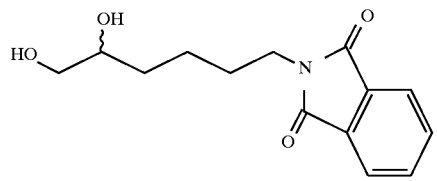
N-(5,6-Dihydroxyhexyl)phthalimide

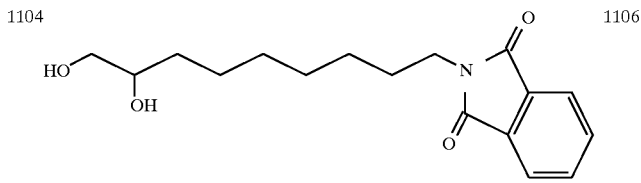
N-(8,9-Dihydroxynonyl)phthalimide

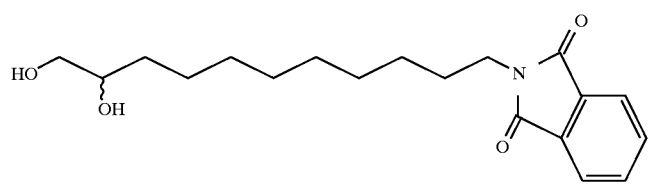
N-(10,11-Dihydroxyundecyl)phthalimide

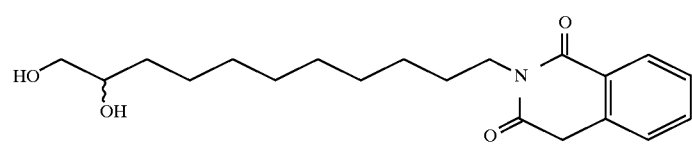
N-(10,11-Dihydroxyundecyl)homophthalimide

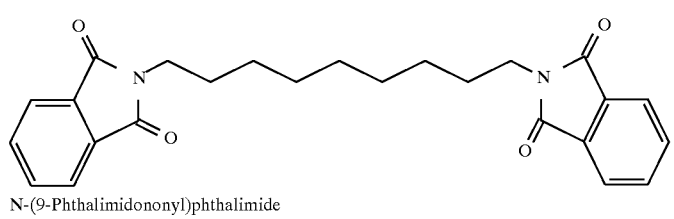
N-(9-Phthalimidononyl)phthalimide

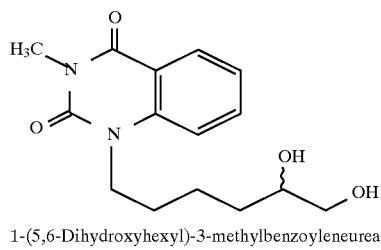
1-(5,6-Dihydroxyhexyl)-3-methylbenzoyleneurea

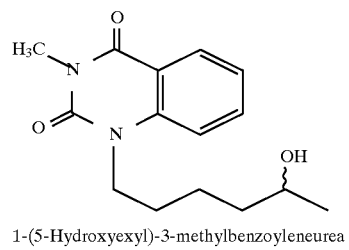
1-(5-Hydroxyexyl)-3-methylbenzoyleneurea

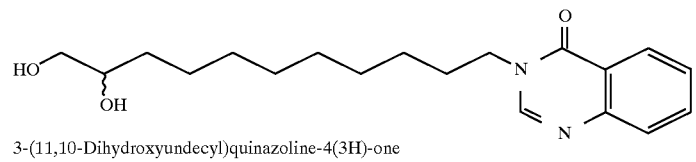
3-(11,10-Dihydroxyundecyl)quinazoline-4(3H)-one

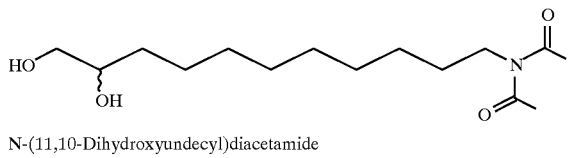
N-(11,10-Dihydroxyundecyl)diacetamide

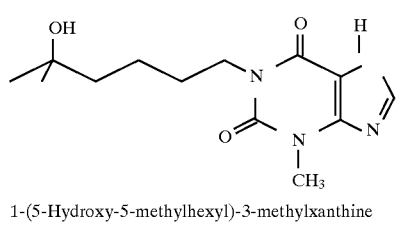
1-(5-Hydroxy-5-methylhexyl)-3-methylxanthine

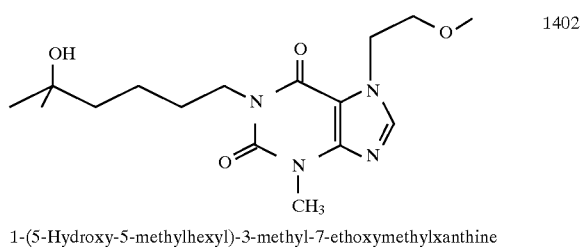
1-(5-Hydroxy-5-methylhexyl)-3-methyl-7-ethoxymethylxanthine

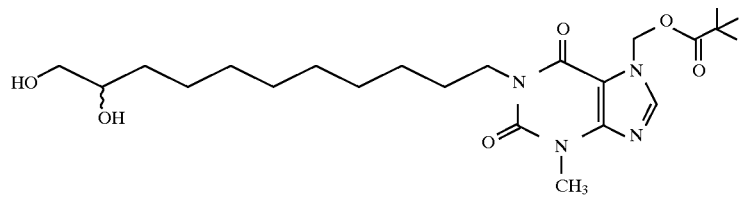
1-(10,11-Dihydroxyundecyl)-3-methyl-7-methylpivaloylxanthine
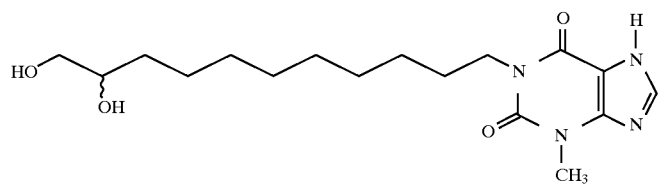
1-(10,11-Dihydroxyundecyl)-3-methylxanthine
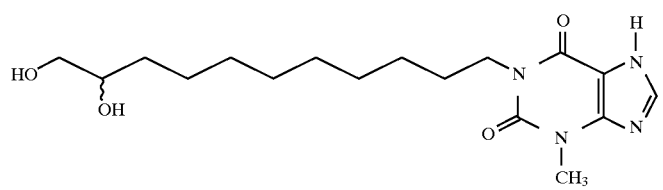
1-(10-Hydroxyundecyl)-3-methylxanthine
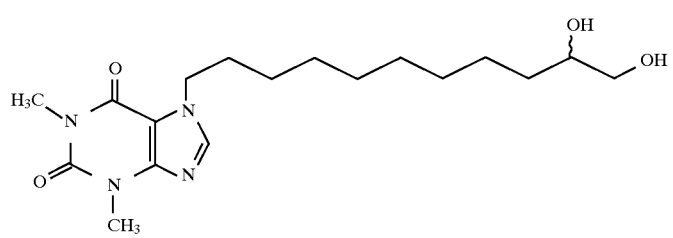
7-(10,11-Dihydroxyundecyl)-1,3-dimethylxanthine
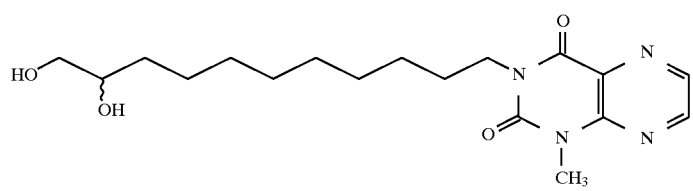
3-(11,10-Dihydroxyundecyl)-1-methyl-2,4-dioxotetrahydropteridine
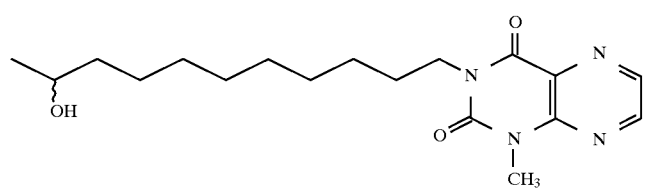
3-(10-Hydroxyundecyl)-1-methyl-2,4-dioxotetrahydropteridine
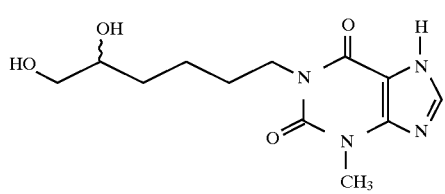
1-(5,6-Dihydroxyhexyl)-3-methylxanthine
1407
1408
1417
1420
1428
1429
1440

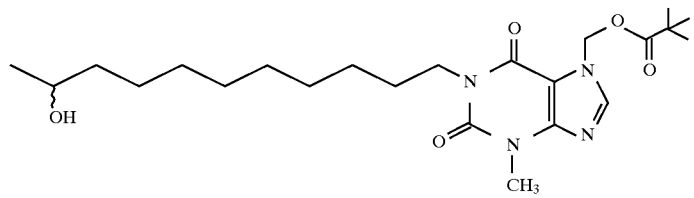

1-(10-Hydroxyundecyl)-3-methyl-7-methylpivaloylxanthine 1444

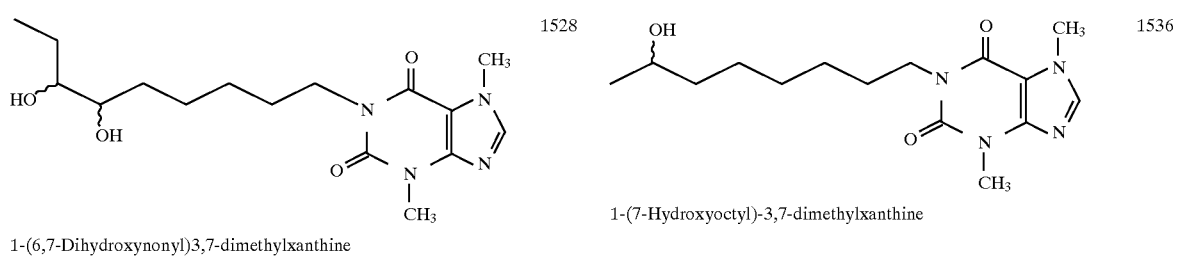

1-(6,7-Dihydroxynonyl)3,7-dimethylxanthine 1528

1-(7-Hydroxyoctyl)-3,7-dimethylxanthine 1536

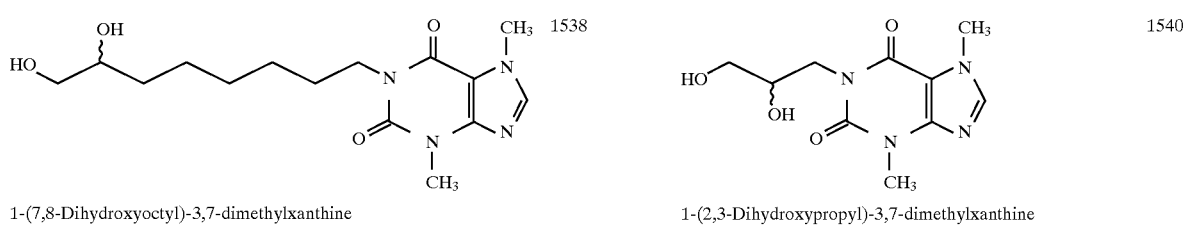

1-(7,8-Dihydroxyoctyl)-3,7-dimethylxanthine 1538

1-(2,3-Dihydroxypropyl)-3,7-dimethylxanthine 1540

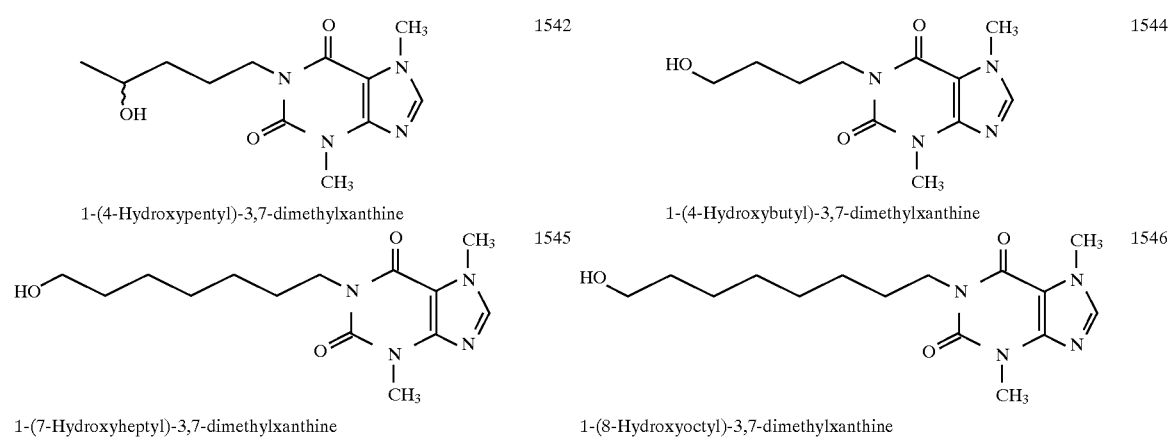

1-(4-Hydroxypentyl)-3,7-dimethylxanthine 1542

1-(4-Hydroxybutyl)-3,7-dimethylxanthine 1544

1-(7-Hydroxyheptyl)-3,7-dimethylxanthine 1545

1-(8-Hydroxyoctyl)-3,7-dimethylxanthine 1546

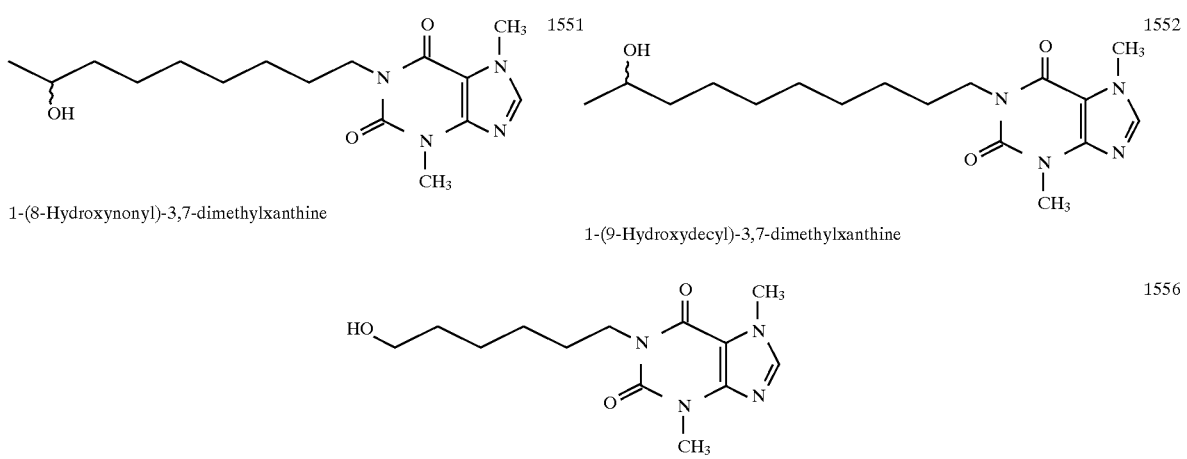

1-(8-Hydroxynonyl)-3,7-dimethylxanthine 1551

1-(9-Hydroxydecyl)-3,7-dimethylxanthine 1552

1-(6-Hydroxyhexyl)-3,7-dimethylxanthine 1556

-continued

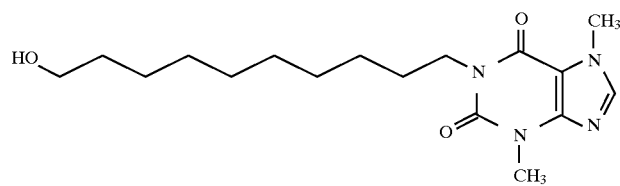

1-(10-Hydroxydecyl)-3,7-dimethylxanthine 1559

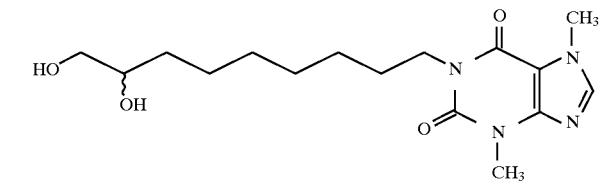

1-(8,9-Dihydroxynonyl)-3,7-dimethylxanthine 1561

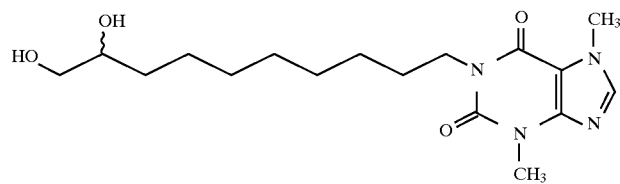

1-(9,10-Dihydroxydecyl)-3,7-dimethylxanthine 1564

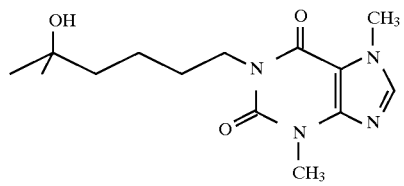

1-(5-Hydroxy-5-methylhexyl)-3,7-dimethylxanthine 1566

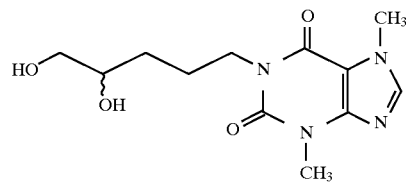

1-(4,5-Dihydroxypentyl)-3,7-dimethylxanthine 1584

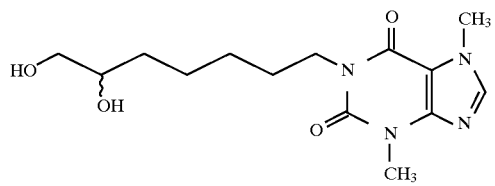

1-(6,7-Dihydroxyheptyl)-3,7-dimethylxanthine 1585

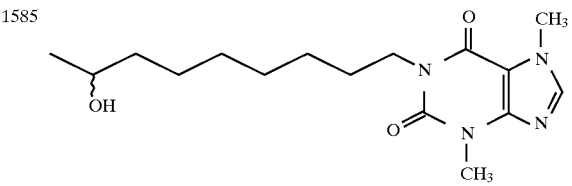

1-(10-Hydroxyundecyl)-3,7-dimethylxanthine 1587

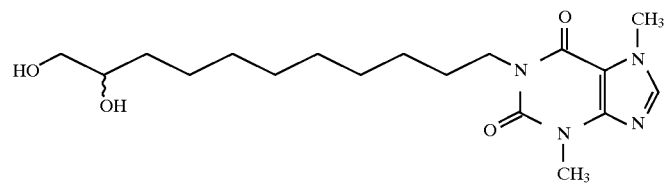

1-(10,11-Dihydroxyundecyl)-3,7-dimethylxanthine 1592

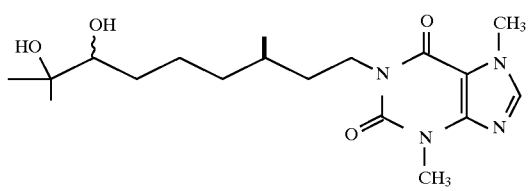

1-(3-(R)-Methyl-7-methyl-6,7-dihydroxyoctyl)-3,7-dimethylxanthine 1597

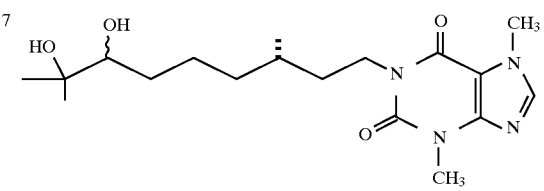

1-(3-(S)-Methyl-7-methyl-6,7-dihydroxyoctyl)-3,7-dimethylxanthine 1597

-continued

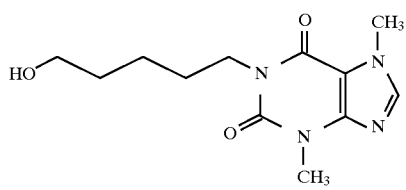

1-(5-Hydroxypentyl)-3,7-dimethylxanthine 1598

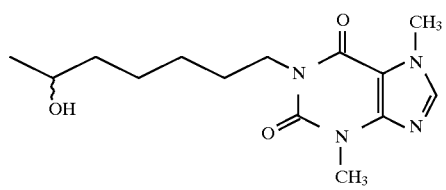

1-(6-Hydroxyheptyl)-3,7-dimethylxanthine 1599

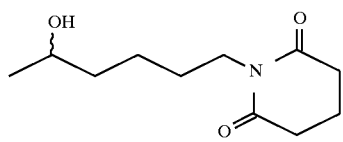

N-(5-Hydroxyhexyl)glutarimide 1601

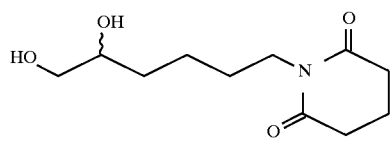

N-(5,6-Dihydroxyhexyl)glutarimide 1603

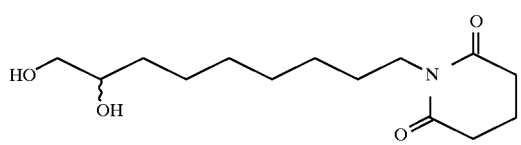

N-(8,9-Dihydroxynonyl)glutarimide 1609

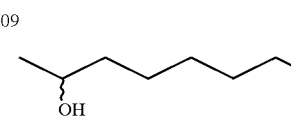

N-(8,9-Dihydroxynonyl)glutarimide 1612

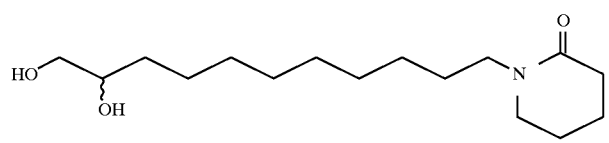

N-(10,11-Dihydroxyundecyl)-2-piperidone 1617

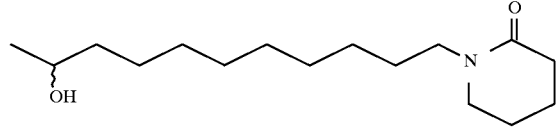

N-(10-Hydroxyundecyl)-2-piperidone 1621

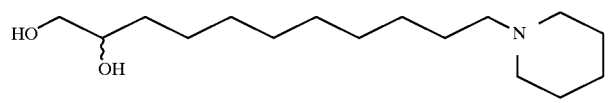

N-(10,11-Dihydroxyundecyl)piperidine 1622

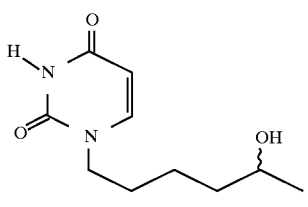

1-(5-Hydroxyhexyl)uracil 1806

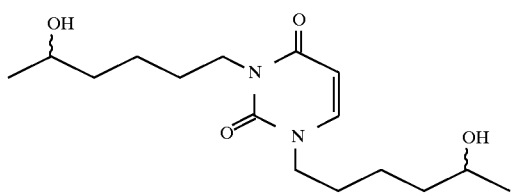

1,3-Bis-(5-Hydroxyhexyl)uracil 1807

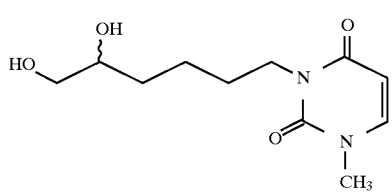

3-(5,6-Dihydroxyhexyl)-1-methyluracil 1811

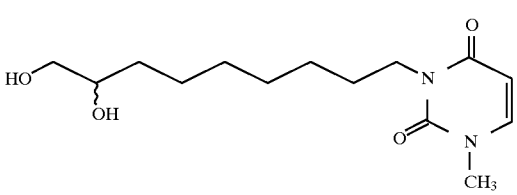

3-(8,9-Dihydroxynonyl)-1-methyluracil 1818

-continued

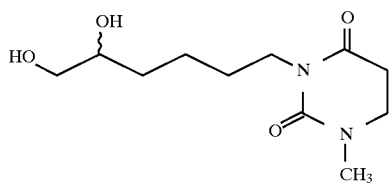
3-(5,6-Dihydroxyhexyl)-1-methyldihydrouracil

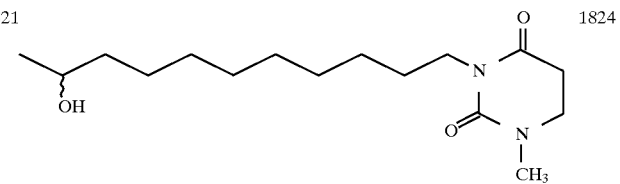
3-(10-Hydroxyundecyl)-1-methyldihydrouracil

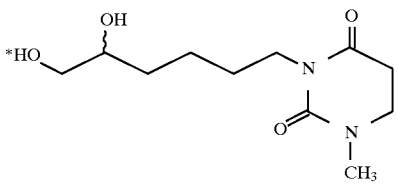
3-(10,11-Dihydroxyundecyl)-1-methyldihydrouacil

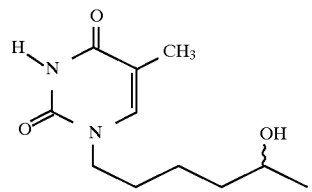
1-(5-Hydroxyhexyl)thymine

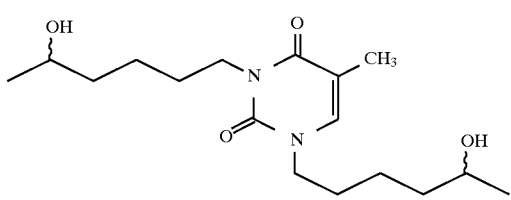
Bis-1,3-(5-Hydroxyhexyl)thymine

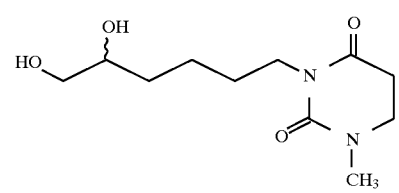
3-(5,6-Dihydroxyhexyl)-1-methylthymine

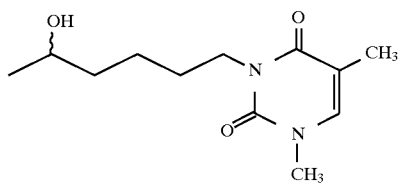
3-(5-Hydroxyhexyl)-1-methylthymine

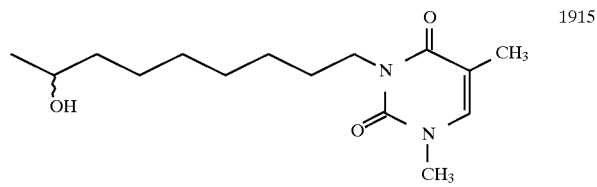
3-(8-Hydroxynonyl)-1-methylthymine

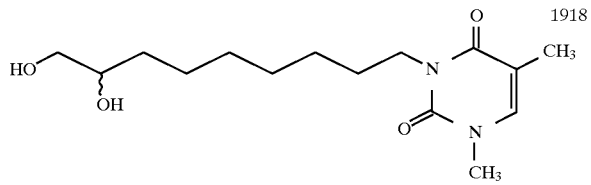
3-(8,9-Dihydroxynonyl)-1-methylthymine

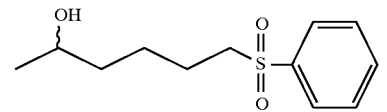
5-(Hydroxyhexyl)phenylsulfone

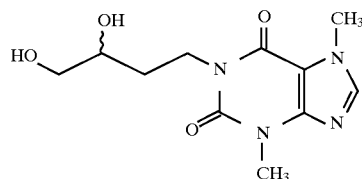
1-(3,4-Dihydroxybutyl)-3,7-dimethylxanthine

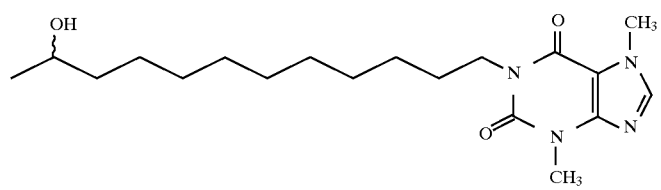
1-(11-Hydroxydodecenyl)-3,7-dimethylxanthine

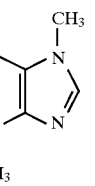

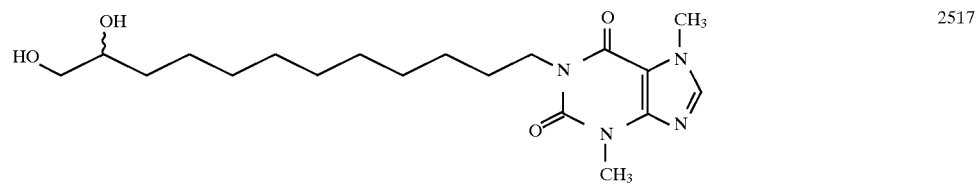
1-(11,12-Dihydroxydodecyl)-3,7-dimethylxanthine
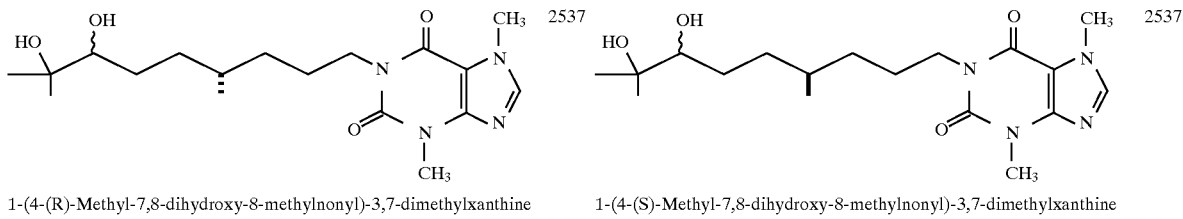
1-(4-(R)-Methyl-7,8-dihydroxy-8-methylnonyl)-3,7-dimethylxanthine    1-(4-(S)-Methyl-7,8-dihydroxy-8-methylnonyl)-3,7-dimethylxanthine
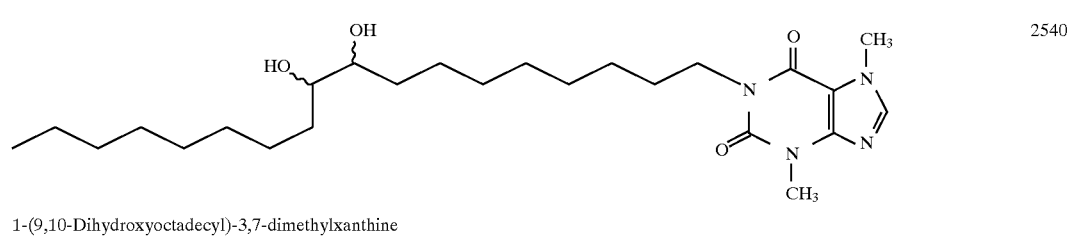
1-(9,10-Dihydroxyoctadecyl)-3,7-dimethylxanthine
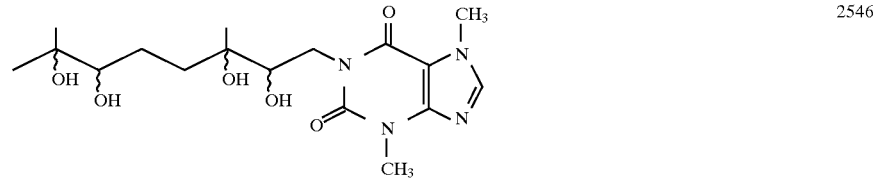
1-(3,7-Dimethyl-2,3,6,7-tetrahydroxyoctyl)-3,7-dimethylxanthine
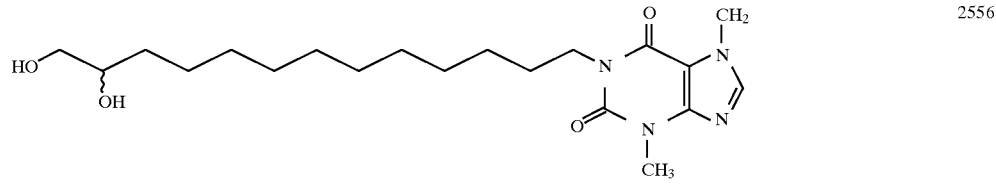
1-(12,13-Dihydroxytridecyl)-3,7-dimethylxanthine
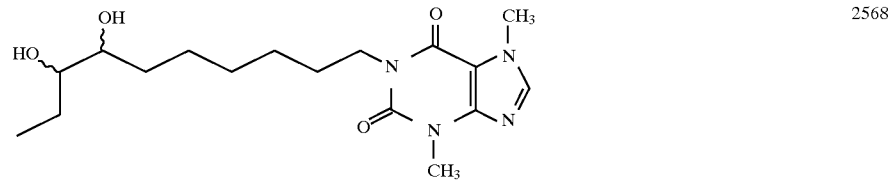
1-(7,8-Dihydroxydecyl)-3,7-dimethylxanthine
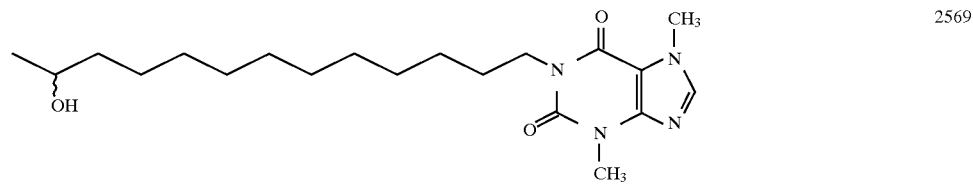
1-(12-Hydroxytridecyl)-3,7-dimethylxanthine -continued
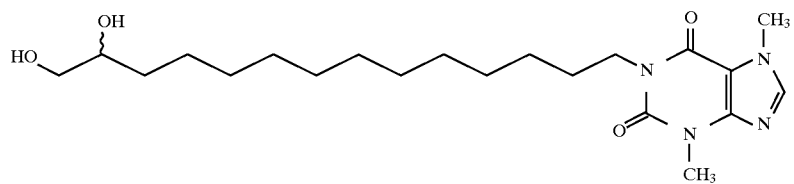
1-(13,14-Dihydroxytetradecyl)-3,7-dimethylxanthine 2595
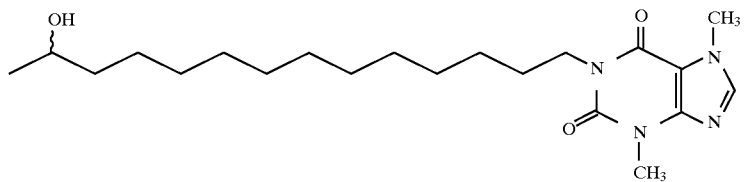
1-(13-Hydroxytetradecyl)-3,7-dimethylxanthine 3504
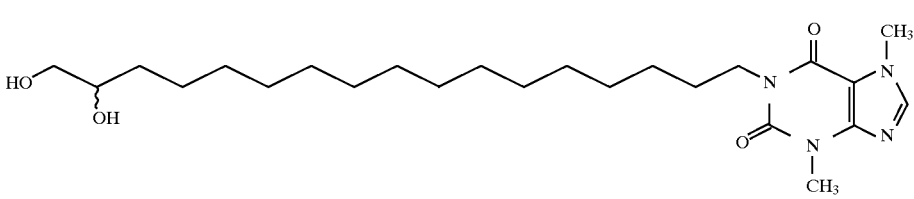
1-(16,17-Dihydroxyheptadecyl)-3,7-dimethylxanthine 3514
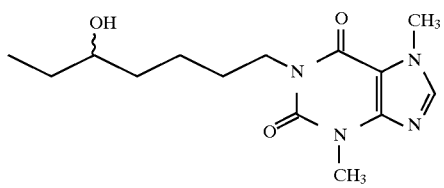
1-(5-Hydroxyheptyl)-3,7-dimethylxanthine 3515
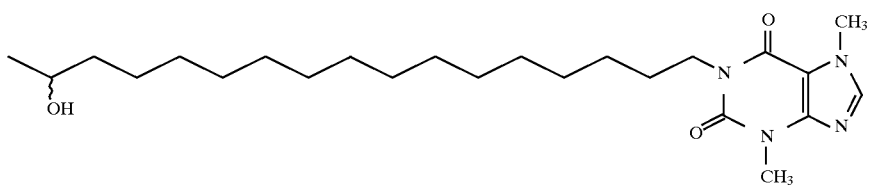
1-(16-Hydroxyheptadecyl)-3,7-dimethylxanthine 3518
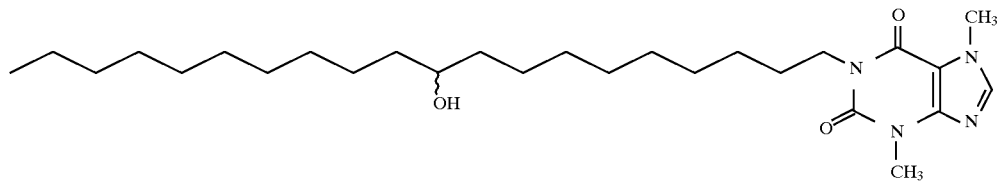
1-(10-Hydroxyeicosyl)-3,7-dimethylxanthine 3520
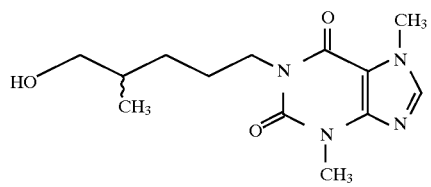
1-(5-Hydroxy-4-methylpentyl)-3,7-dimethylxanthine 3524
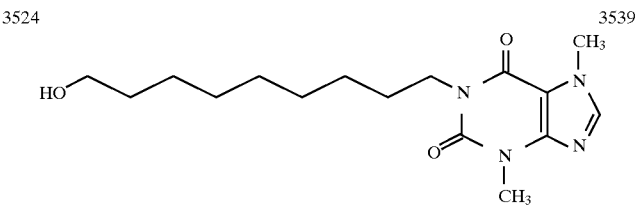
1-(9-Hydroxynonyl)-3,7-dimethylxanthine 3539

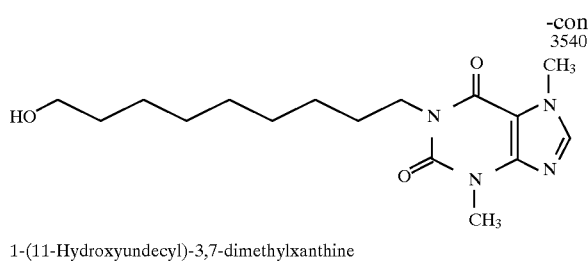

1-(11-Hydroxyundecyl)-3,7-dimethylxanthine

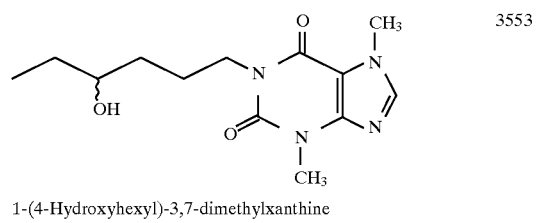

1-(4-Hydroxyhexyl)-3,7-dimethylxanthine

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to the inhibition of a degradation pathway for the compounds of the invention; in particular with respect to dealkylation at the N7 position of the xanthine core. For example, NIH3T3-D5C3 cells can be used to compare effects of a compound of Formula 1 alone or in combination with a P-450 inhibitor by comparing transformation phenotype among control, incubation with a compound of Formula 1 alone, and coincubation of a compound of Formula 1 with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

The following examples, which should not be regarded as limiting in any way, illustrate the invention. In these examples PTX means Pentoxifylline.

EXAMPLE 1

This example illustrates a method for synthesis of compound no. 1551. The synthesis began with a solution of 8-nonene-1-ol (3.52 mmol, 0.5 g) in 30 ml of dichloromethane. Methanesulfonyl chloride (3.52 mmol, 0.4 g, 270 μl) was added with stirring at 0° C., followed by an addition of triethylamine (5.28 mmol, 0.534 g, 736 μl). The mixture was warmed to room temperature over an hour and then was poured into 50 ml of saturated aqueous sodium bicarbonate solution. The organic layer was washed with an equal volume of brine, dried over magnesium sulfate, filtered and the solvent evaporated to give a mesylate, which was taken up in 10 ml of DMSO (dimethylsulfoxide).

A mixture of theobromine (3.52 mmol, 0.63 ), stirring in 20 ml DMSO, was added to sodium hydride (3.87 mmol, 93 mg). After 1 hour of vigorous stirring, the mesylate in 10 ml of DMSO was added to this viscous mixture. The mixture became less viscous as the reaction proceeded. After 54 hours of stirring, the mixture was poured into water (50 ml) and extracted with diethylether (3×50 ml) followed by dichloromethane (4×40 ml). After the dichloromethane was evaporated, a remaining brown oil residue was purified using chromatography on silica with ethylacetate, yielding 530 mg of 1-(8-nonene)3,7-dimethylxanthine as an off-white powder (50% yield).

1-(8-nonene)-3,7-dimethylxanthine (380 mg, 1.25 mmol) was dissolved in 1 ml water and then 1 ml of concentrated sulfuric acid was added at once. This mixture was stirred for 24 hours. The reaction mixture was poured over 50 ml water and extracted with dichloromethane (3×50 ml). The dichloromethane extractions were combined and dried over magnesium sulfate, and evaporated to yield a viscous oil. Recrystalization from minimal dichloromethane/excess diethyl ether yielded 110 mg of 1-(8-hydroxynonyl)-3,7-dimethylxanthine (0.34 mmol, 27% yield). However, this ω-1 alcohol preparation also contained a significant concentration of a contaminating ω-2 alcohol, (1-(7-hydroxynonyl)-3,7-dimethylxanthine), which is also a compound within the scope of Formula II.

EXAMPLE 2

This example illustrates a synthesis procedure for compound no. 1564 (see compound names and structures above). The synthesis began with a solution of 9-decene-1-ol (3.0 g, 19.2 mmol) in dichloromethane (100 ml) at 0° C. To this solution was added methanesulfonyl chloride (2.2 g, 1.5 ml, 19.2 mmol), followed by triethylamine (2.91 g, 28.8 mmol). After stirring for 15 minutes at 0° C., the reaction mixture was allowed to warm to room temperature. After 2 hours, the reaction mixture was poured into 100 ml of water and extracted with dichloromethane (3×60 ml). The organic portions were combined, dried in sodium sulfate, and evaporated to give 9-decene-1-mesylate as a yellow oil (4.52 g, 100% yield). The mesylate was used without further purification.

Theobromine (3.45 g, 19.2 mmol) was added to a suspension of NaH (461 mg, 19.2 mmol) in DMSO (30 ml). After 15 minutes, 9-decene-1-methanesulfonate (2.25 g, 11 mmol) was added and the reaction mixture was stirred for 18 hours at 25° C., and then at 100° C. for 40 minutes. The reaction mixture was poured into 100 ml of water and extracted with dichloromethane (3×50 ml). The organic portions were combined, washed with brine (60 ml), dried with magnesium sulfate, and evaporated to provide a white solid. Recrystalization of this solid (in dichloromethane/ petroleum ether) provided 3.40 g of a colorless oil, 1-(9-decenyl)-3,7-dimethylxanthine (56% yield).

A solution of 1-(9-decenyl)-3,7-dimethylxanthine, prepared according to the foregoing procedure (3.2 g, 10.1 mmol), 4-methylmorpholine-N-oxide (1.41 g, 12 mmol) and $OsO_4$ (3 drops of a 2.5% solution by weight in tBuOH) in acetone (40 ml) and water (10 ml) was stirred for 24 hours. A saturated solution of sodium dithionite (5 ml) was added to the reaction mixture which was then stirred for 15 minutes. The reaction mixture was extracted with 25% EtOH/dichloromethane (4×50 ml). The organic layers were combined, dried with sodium sulfate and evaporated, leaving a white solid which was recrystalized in ethanol, resulting in 3.3 g of compound no. 1564 (93% yield).

EXAMPLE 3

This example illustrates a synthesis for compound no. 1552. The synthesis begins with a solution of compound no. 1564 [1-(9,10-dihydroxydecyl-3,7-dimethylxanthine (2.11 g, 6.0 mmol)] from Example 2. Compound no. 1564 was stirred with HBr (5.38 ml, 4.85 g of a 30% solution in acetic acid, 18 mmol) for 90 minutes. The mixture was added to a flask containing saturated aqueous sodium bicarbonate solution (40 ml) and 50 ml of dichloromethane. After 10 minutes of vigorous stirring, the layers were separated and the aqueous layers washed with dichloromethane (2×50 ml). The organic portions were combined, dried with sodium sulfate, and evaporated to give 1-(9'-acetoxy-10'-bromodecyl)-3,7-dimethylxanthine as a yellow oil (2.72 g, 100% yield). Without further purification, the oil was taken up in methanol (30 ml), and treated with a solution of sodium methoxide (prepared from 151 mg, 6.6 mmol sodium and 6 ml methanol). After 30 minutes, the reaction mixture was added to water (30 ml) and extracted with dichloromethane (3×50 ml). The organic layers were combined and dried with sodium sulfate to give an off-white solid which was recrystalized (in dichloromethane/ petroleum ether) to yield 1-(9,10-oxidodecyl)-3,7-dimethylxanthine racemic mixture.

A solution of 1-(9,10-oxidodecyl)-3,7-dimethylxanthine (200 mg, 0.6 mmol) and sodium borohydride (61 mg, 1.6 mmol) was stirred in ethanol (10 ml) at 80° C. for 4 hours. After cooling, the reaction mixture was poured into 10 ml of saturated aqueous ammonium chloride. Water (10 ml) was added to dissolve any solids that were formed and the mixture was extracted with dichloromethane (3×50 ml). The organic extracts were combined, dried with sodium sulfate, and evaporated to an off-white solid. The solid was recrystalized ( in dichloromethane/petroleum ether), resulting in 180 mg of a racemic mixture of compound no. 1552, a white solid (89% yield).

EXAMPLE 4

This example illustrates a synthesis procedure for compound no. 1561 (chemical name and structure above). The synthesis began by adding a solution of 8-nonene-1-ol (1.50 g, 10.5 mmol) in dichloromethane (100 ml) at 0° C. to methanesulfonyl chloride (1.20 g, 813 μl, 10.5 mmol), followed by triethylamine (1.59 g, 15.8 mmol). After stirring for 1 hour at 0° C., the reaction mixture was allowed to warm to room temperature. The reaction mixture was poured into 100 ml of water and extracted with dichloromethane (3×50 ml). The organic portions were combined, dried with sodium sulfate, and evaporated, resulting in 2.25 g of 9-methanesulfonyl-1-nonene, a yellow oil (97% yield), which was used without further purification.

Theobromine (1.98 g, 11 mmol) was added to a suspension of NaH (600 mg of a 50% mineral oil slurry, 12 mmol)

in DMSO (15 ml). After 15 minutes, 9-methanesulfonyl-1-nonene, prepared according to the foregoing procedure (2.25 g, 11 mmol), was added and the reaction mixture stirred for 6 days at 25° C. The reaction mixture was poured into 60 ml of water and extracted with dichloromethane (3×50 ml). The organic portions were combined, dried with magnesium sulfate, and evaporated to give a dark oil. Chromatography over silica gel using an ethyl acetate eluant produced 810 mg of 1-(8-nonenyl)-3,7-dimethylxanthine, a colorless oil (26% yield).

A solution of 1-(8-nonenyl)-3,7-dimethylxanthine (810 mg, 2.9 mmol), 4-methylmorpholine-N-oxide (340 mg, 2.9 mmol) and $OsO_4$ (3 drops of a 2.5% solution by weight in tBuOH) in acetone (20 ml) and water (20 ml) was stirred for 24 hours. A saturated solution of sodium dithionite (5 ml) was added to the reaction mixture, which was subsequently stirred for 15 minutes. The reaction mixture was extracted with 25% EtOH/dichloromethane (4×50 ml). The organic layers were combined, dried with sodium sulfate and evaporated, leaving a white solid. Recrystalized of the white solid in ethanol/chloroform resulted in 490 mg of compound no. 1561 (54% yield).

EXAMPLE 5

This example illustrates another method for synthesizing compound no. 1551 (in addition to the method described in Example 1). 1-(8,9-dihydroxynonyl)-3,7-dimethylxanthine (compound no. 1561, 428 mg, 1.3 mmol) was stirred with HBr (777 μl, 1.05 g of a 30% solution in acetic acid, 3.9 mmol) for 90 minutes. The mixture was then added to a flask containing aqueous sodium bicarbonate solution (10 ml, 1.35 g) and dichloromethane (10 ml) and stirred vigorously for 10 minutes. The layers were separated and the aqueous portion was washed with dichloromethane (3×15 ml). The organic portions were combined, dried with sodium sulfate and evaporated to give 1-(8-acetoxy-9-bromononyl)-3,7-dimethylxanthine as a yellow oil (550 mg, 96% yield). Without further purification, the oil was taken up in methanol (5 ml) and treated with a solution of sodium methoxide (prepared from 33 mg, 1.4 mmol sodium and 1.4 ml methanol). After 30 minutes, the reaction mixture was added to water (30 ml) and extracted with dichloromethane (3×40 ml). The organic portions were combined and dried to give an off-white solid. Recrystalization of the remaining solid was recrystalized in dichloromethane/petroleum ether, resulting in 380 mg of 1-(8,9-oxidononyl)-3,7-dimethylxanthine (91% yield).

100 mg of 1-(8,9-oxidononyl)-3,7-dimethylxanthine (0.3 mmol) was dissolved in methanol (20 ml). Palladium catalyst (10% on carbon, 100 mg) was added and the slurry was placed under hydrogen (50–55 psi) on a Parr reactor for 16 hours. The slurry was filtered through celite, evaporated to a yellow oil and purified using chromatography over silica gel using 10% ethanol/ethyl acetate eluant, producing 53 mg of compound no. 1551, a white solid (55% yield).

EXAMPLE 6

This example illustrates a synthesis for compound no. 1559. A mixture of theobromine (1.0 g, 5.5 mmol) and 50% NaH in oil (264 mg, 5.5 mmol) in DMSO (35 ml) was stirred for 5 minutes and then 10-bromodecane-1-ol (1.3 g, 5.5 mmol) was added and stirred for 14 hours. The solution was treated with water (100 ml) and extracted with ether (2×50 ml). The heterogeneous aqueous phase was extracted with dichloromethane (3×30 ml). The combined organic layers were washed with water (2×100 ml), dried with magnesium sulfate, and the dichloromethane was evaporated under vacuum, resulting in 1.6 g of compound no. 1559, a white powder (87% yield).

EXAMPLE 7

This example illustrates a synthesis of compound no. 1545 (see above for chemical name and structure). Sodium hydride (95% 840 mg, 35 mmol) was added to a solution of theobromine (2.88 g, 16 mmol) in dimethylsulfoxide (50 ml). After 20 minutes of stirring, 7-bromoheptanol (2.92 g, 15 mmol) was added. The reaction mixture was warmed to 60° C. and stirred for 16 hours at 60° C. The reaction was poured into a separatory funnel containing 100 ml of saturated $NH_4Cl$ solution and extracted with dichloromethane (3×100 ml). The organic portions were combined, washed with water (2×100 ml) and brine (100 ml), dried over anhydrous magnesium sulfate and concentrated under reduced pressure. The resulting crude product was purified by flash chromatography over silica gel using an ethyl acetate eluent, producing 2.58 g of compound no. 1545 (58% yield).

EXAMPLE 8

This example illustrates a synthesis for compound no. 1592. Sodium hydride(95%, 1.26 g, 50 mmol) was added to a solution of theobromine (7.2 g, 40 mmol) in dimethylsulfoxide (300 ml). After 20 minutes of stirring, undecenylmesylate (7.95 g, 30 mmol) was added and the resulting mixture stirred for 12 hours at room temperature. The reaction was warmed to 70°–80° C. and stirred for 4 hours. The reaction mixture was then poured into a separatory funnel containing 1 L of water and extracted with dichloromethane (5×200 ml). The organic extracts were combined, washed with water (100 ml) and brine (100 ml), dried over anhydrous magnesium sulfate and concentrated under reduced pressure. The crude product obtained was further purified by flash chromatography over silica gel using 20% hexane and dichloromethane eluent, producing 4.6 g of 1-(10-undecenyl)-3,7-dimethylxanthine (46.3% yield).

A solution of 1-(10-undecenyl)-3,7-dimethylxanthine, prepared in the foregoing procedure (4.3 g, 13 mmol), 4-methylmorpholine-N-oxide (1.942 g, 16.6 mmol), and potassium osmate dihydrate (9.5 mg; 0.026 mmol) in acetone (45 ml) and water (10 ml) was stirred for 6 hours. A solution of 20% aqueous sodium sulphite (12 ml) was added and the resulting mixture stirred for 30 minutes. The reaction mixture was extracted with 25% ethanol/dichloromethane (4×100 ml). The combined organic extracts were dried over anhydrous magnesium sulfate, concentrated under reduced pressure and purified by flash chromatography over silica gel using a methanol (5%)/dichloromethane eluent, producing 3.6 g of compound no. 1592 (76% yield).

EXAMPLE 9

This example illustrates a synthesis for compound no. 1587 (see above for chemical name and structure). Compound no. 1592 [(10,11-dihydroxyundecanyl)-3,7-dimethylxanthine] as prepared above (3.6 g, 10 mmol) was stirred with hydrogen bromide (6.2 ml, 8.4 g of a 30% solution in acetic acid, 31.1 mmol) for 90 minutes. The mixture was then added to a flask containing 100 ml aqueous sodium bicarbonate solution and 75 ml dichloromethane. After 10 minutes of vigorous stirring the layers were separated and the aqueous portion washed with dichloromethane (3×75 ml). The organic portions were combined, dried over magnesium sulfate, and evaporated, yielding 3.6 g of 1-(10-acetoxy-11-bromoundecanyl)-3,7-dimethylxanthine. Without further purification, the bromoacetate was taken up in methanol (25 ml) and treated with a solution of sodium methoxide (prepared from 0.28 g, 12.2 mmol sodium, and 25 ml methanol). After 30 minutes, most of the solvent was removed under reduced pressure and the residue extracted with dichloromethane (3×75 ml). The organic portions were combined, dried over magnesium sulfate and concentrated under reduced pressure, resulting in an off-white solid. The solid was purified by column chromatography over silica gel using dichloromethane/(3%) methanol eluant, producing 2.0 g of 1-(10,11-oxidoundecanyl)-3,7-dimethylxanthine (57.5% yield)

348 mg (1 mmol) 1-(10,11-oxidoundecanyl)-3,7-dimethylxanthine, prepared according to the forgoing procedure was added to a suspension of sodium borohydride (115.6 mg; 3 mmol) in 10 ml of ethanol. The reaction was warmed to 60° C. and stirred overnight. Most of the ethanol was removed under reduced pressure, at standard ambient temperature. 20 ml of NH4Cl solution was added and extracted with ethyl acetate (3×75 ml). The combined organic extracts were dried over anhydrous magnesium sulfate and concentrated under reduced pressure. The resulting crude product was purified by flash chromatography over silica gel using 3% methanol/dichloromethane eluant, producing 237 mg of compound no. 1587 (68% yield).

EXAMPLE 10

This example illustrates a process for making compound no. 1596. Sodium hydride(95%, 631 mg, 25 mmol) was added to a solution of theobromine (4.14 g, 23 mmol) in dimethylsulfoxide (75 ml). After 20 minutes of stirring, (R)(–)citronellyl bromide (5.0 g, 22.8 mmol) was added. After 16 hours of stirring the resulting mixture at room temperature, the reaction was poured into a separatory funnel containing 500 ml of water and extracted with dichloromethane (3×100 ml). The organic extracts were combined, washed with water (100 ml) and brine (100 ml), dried over anhydrous magnesium sulfate and concentrated under reduced pressure. The resulting crude product was purified by flash chromatography over silica gel using 30% petroleum ether/ethyl acetate eluant, producing 5.9 g of compound no. 1596, a yellowish oil (81.5% yield).

EXAMPLE 11

This example illustrates a synthesis of compound no. 1824. Sodium hydride (288 mg, 12 mmol) was added to a solution of N-methylhydrouracil (1.54 g, 12 mmol) and 1-bromo-10-undecene (2.33 g, 10 mmol) in 20 ml of dimethyl sulfoxide at room temperature and stirred for 12 hours. The reaction mixture was then quenched with water (80 ml) and extracted with dichloromethane (3×100 ml). The combined organic extract was washed with saturated aqueous saturated salt solution solution (50 ml), dried over anhydrous magnesium sulfate and concentrated under reduced pressure. The resulting crude product was purified by flash chromatography over silica gel using 20% acetone/hexane eluant, producing 2.04 g 3-(10-undecenyl)-1-methylhydrouracil (61.8% yield).

A solution of 0.28 g (1 mmol) 3-(10-undecenyl)-1-methylhydrouracil, prepared as above, and 0.517 g (1.5 mmol) m-chloroperoxybenzoic acid (50% by wt.) in dichloromethane (6 ml) was stirred for 5 hours. The reaction mixture was diluted with 75 ml of dichloromethane and successively washed with 20% aqueous sodium sulphite solution(25 ml), saturated sodium bicarbonate solution (25 ml), water (25 ml) and aqueous saturated salt solution (25 ml), dried over anhydrous magnesium sulfate and concentrated under reduced pressure. The resulting crude product was purified by flash chromatography over silica gel using 20% acetone/ hexane eluant, producing 0.22 g of 3-(10,11-oxidoundecanyl)-1-methylhydrouracil (74.3% yield).

600 mg (2.03 mmol) of 3-(10,11-oxidoundecanyl)-1-methylhydrouracil was added to a suspension of sodium borohydride (230 mg, 6.1 mmol) in 10 ml of ethanol. The reaction was warmed to 60° C. and stirred overnight. Most of the ethanol was removed under reduced pressure, at standard ambient temperature. Ammonium chloride solution (20 ml) was added and the reaction mixture extracted with ethyl acetate (3×75 ml). The combined organic extracts were dried over anhydrous magnesium sulfate and concentrated under reduced pressure. The resulting crude product was further purified by flash chromatography over silica gel using 30% acetone/hexane eluant, producing 594 mg of compound no. 1824 (92.8% yield).

EXAMPLE 12

This example illustrates the effect of compounds nos. 1551 and 1559 as an immune modulator. FIG. 1 shows a mixed lymphocyte reaction of PTX and two inventive compounds nos. 1551 and 1559 (see above for chemical names and structures). The mixed lymphocyte reaction shows a proliferative response of PBMC (peripheral blood mononuclear cells) to allogeneic stimulation determined in a two-way mixed lymphocyte reaction, described above. Each of the inventive compounds tested was more effective and more potent than PTX in this immune modulating activity assay procedure.

EXAMPLE 13

Figure 2:
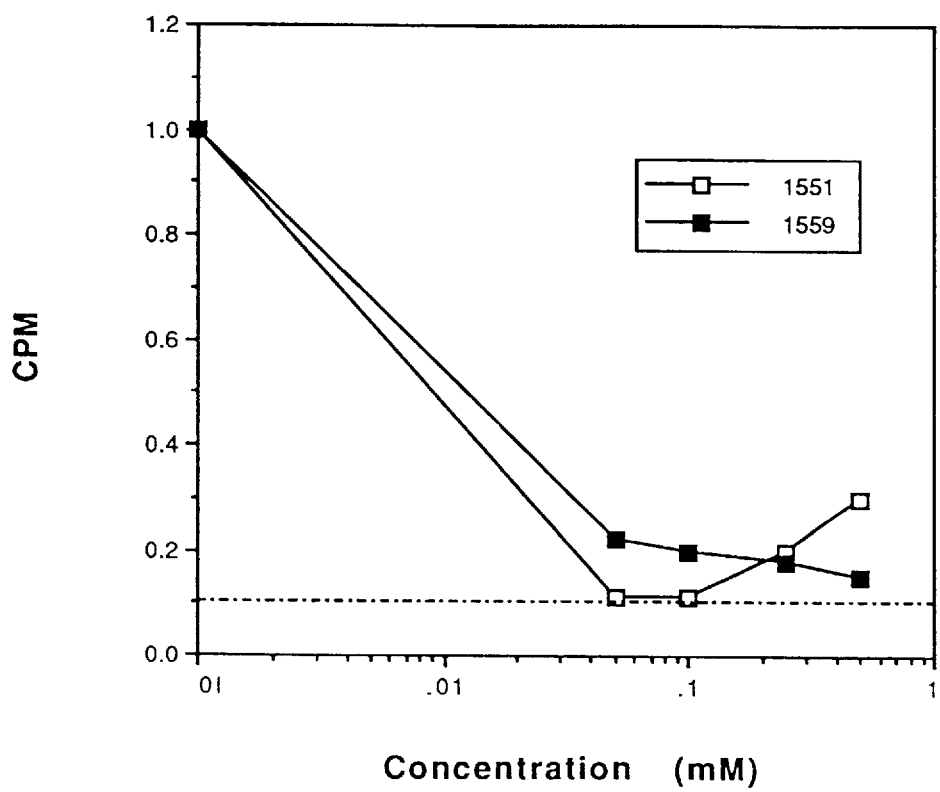
FIG. 2 shows a comparison of inventive compounds nos. 1551 and 1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Both inventive compounds 1551 and 1559 inhibited PDGF-induced stimulation.

This example illustrates a comparison of compounds nos. 1551 and 1559 on PDGF-induced (platelet derived growth factor) proliferation of human stromal cells. Human stromal cells were starved in serum-free media for 24 hours and then stimulated with 50 ng/ml of PDGF-BB. The drugs were added at various indicated concentrations one hour prior to PDGF stimulation. Tritiated thymidine was added at the time of PDGF stimulation. The cells were harvested and counted by liquid scintillation 24 hours after stimulation with PDGF. As shown in FIG. 2, both compound nos. 1551 and 1559 inhibited PDGF-induced stimulation. Background counts (i.e., starved cells) were approximately 10% of control levels.

EXAMPLE 14

Figure 3:
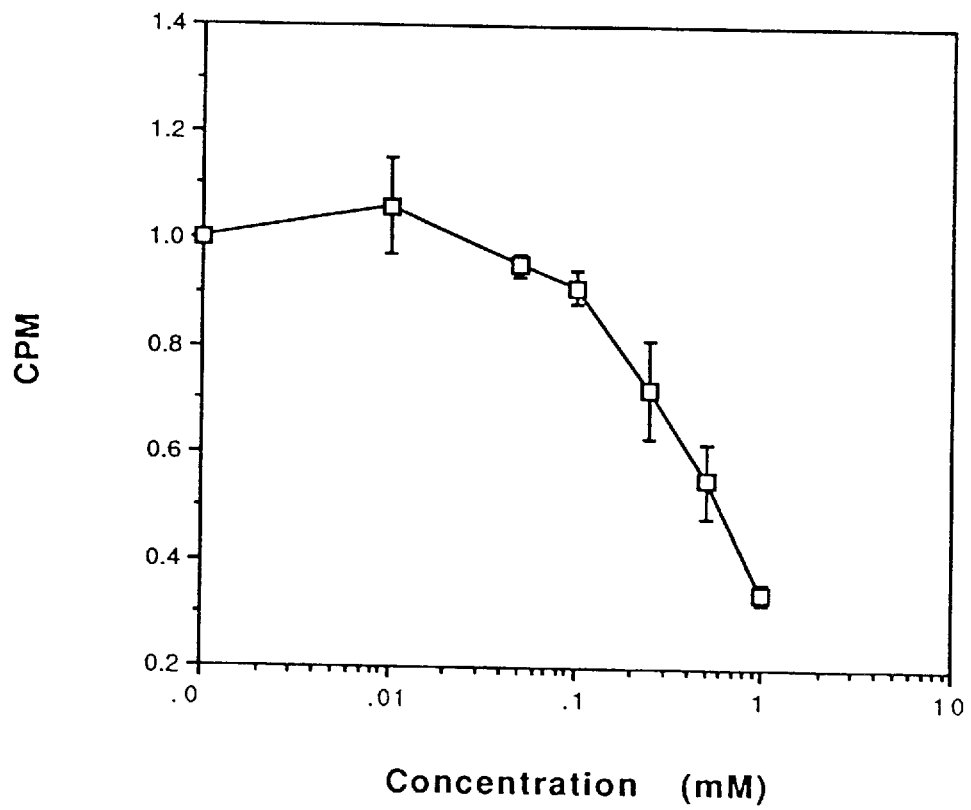
FIG. 3 shows cytotoxicity of inventive compound no. 1559 on LD-2 cells, a human malignant melanoma cell line. The cells were treated with various concentrations of inventive compound no. 1559 and later stained for cell viability with a fluorescent stain. Inventive compound no. 1559 is cytotoxic at higher concentrations, and thus shows anti-tumor activity.

This example provide data from an experiment measuring compound no. 1559 cytotoxicity on LD-2 cells, a human malignant melanoma cell line. The cells were treated with various concentrations of compound no. 1559 and later stained for cell viability with a fluorescence stain (BCECF) and analyzed using a Milipore fluorescence plate reader. As shown in FIG. 3, compound no. 1559 is cytotoxic at higher concentrations, and thus shows antitumor activity.

EXAMPLE 15

Figure 4:
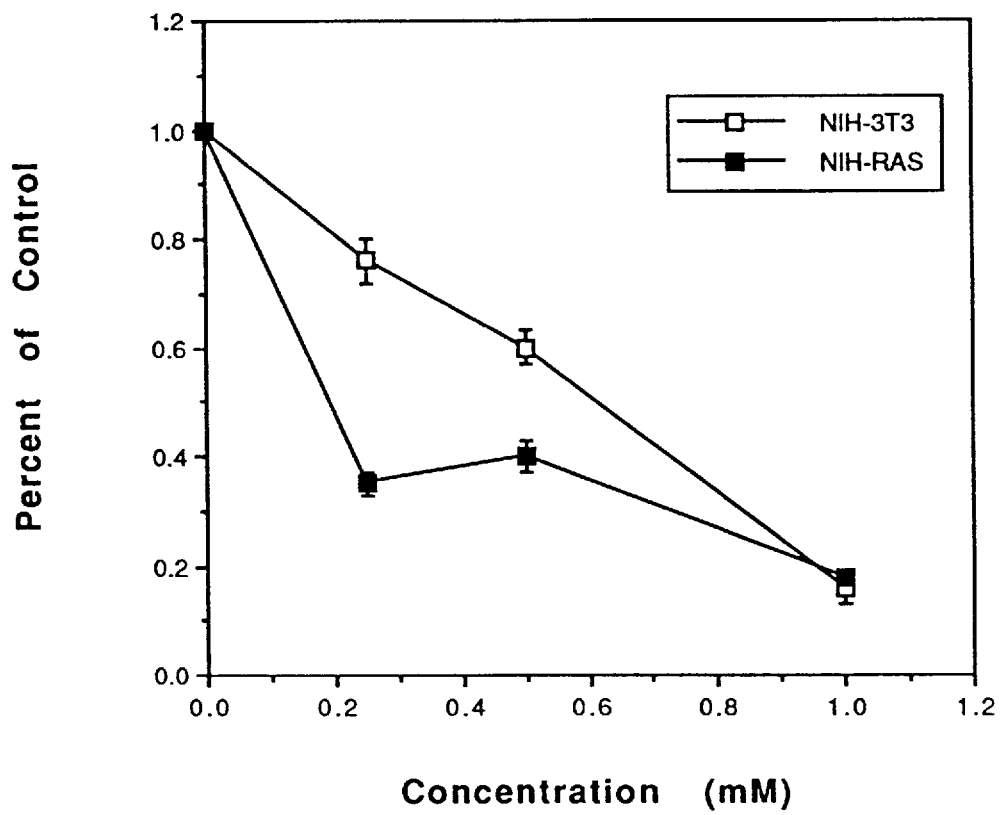
FIG. 4 shows cytotoxicity of inventive compound no. 1559 on NIH-3T3 cells and their Ras transformed counterpart, NIH-3T3 Ras cells. The cells were treated with various concentrations of compound no. 1559 and later stained for cell viability with a fluorescent stain. Compound no. 1559 is cytotoxic at higher concentrations, and thus shows anti-tumor activity.
Figure 5B:
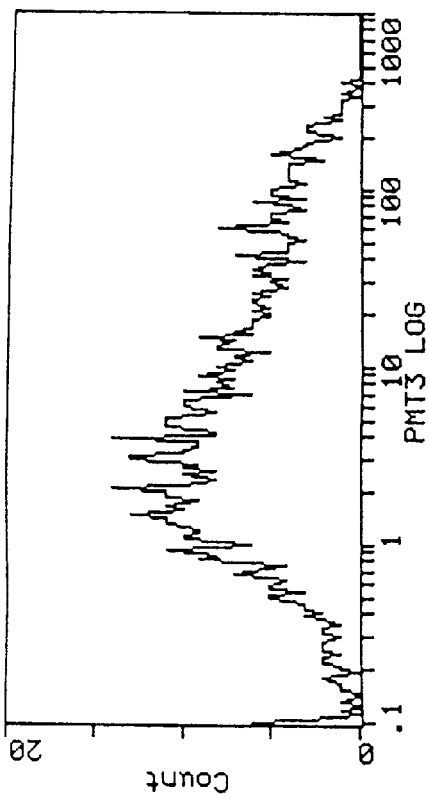
FIG. 5 shows the effect of compound no. 1559 to inhibit cell surface expression of VCAM in human umbilical vein endothelial cells (HUVEC).
Figure 5D:
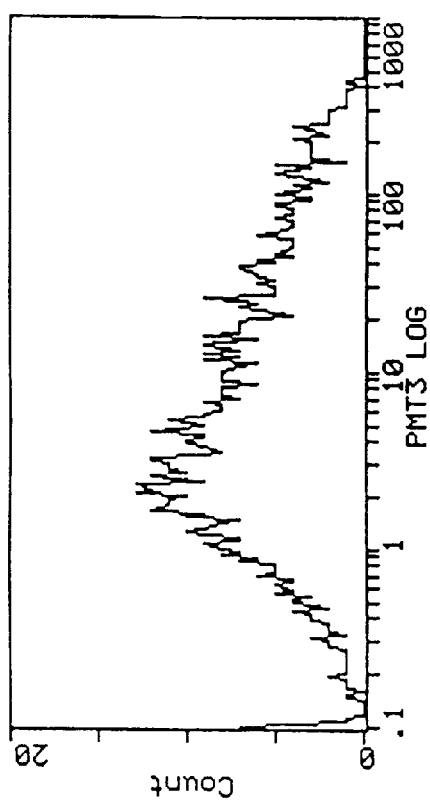
Figure 5A:
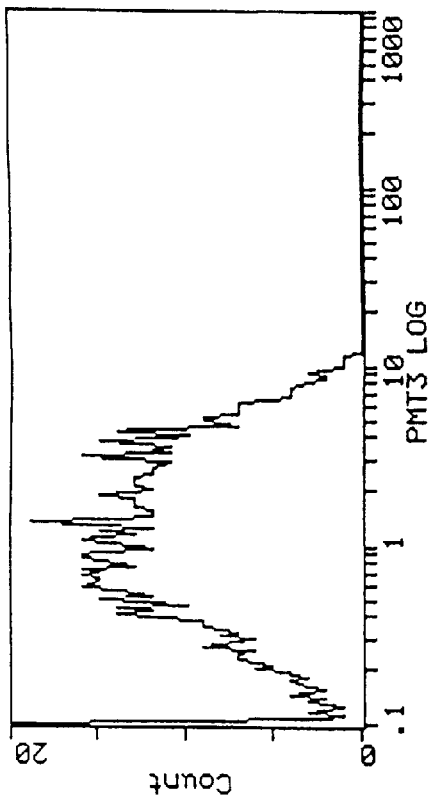
Figure 5C:
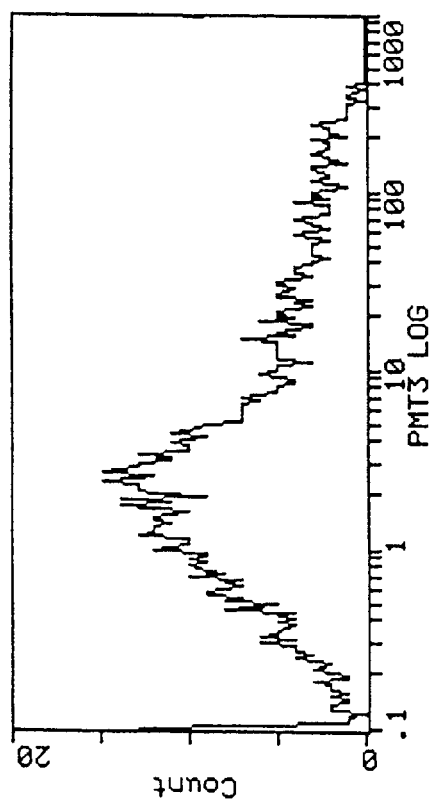

This example provides data from an experiment measuring compound no. 1559 cytotoxicity on NIH-3T3 cells and their Ras transformed counterpart, NIH-3T3 Ras cells. The cells were treated with various concentrations of compound no. 1559 and later stained for cell viability with a fluorescence stain (BCECF) and analyzed using a Milipore fluorescence plate reader. As shown in FIG. 4, compound no. 1559 is cytotoxic at higher concentrations, and thus shows antitumor activity.

EXAMPLE 16

This example illustrates the effect of compound no. 1559 on inhibiting cell surface expression of VCAM in human umbilical vein endothelial cells (HUVEC). The HUVEC cells were stimulated with 20 ng/ml TNF-A for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 5 shows the flow cytometric frequency histograms plotting cell number versus relative fluorescence intensity. The top left histogram is non-TNF induced expression of VCAM (% of cells in gate A is 0.4%). The top right shows cells treated with TNF (% of cells in gate B is 34.5%). The lower left shows cells treated with compound no. 1559 (0.25 mM), one hour prior to TNF addition (% of cells in gate C is 24%). In the lower left, cells treated have been treated with PTX for comparison (% of cells in gate D is 36.8%).

EXAMPLE 17

Figure 6:
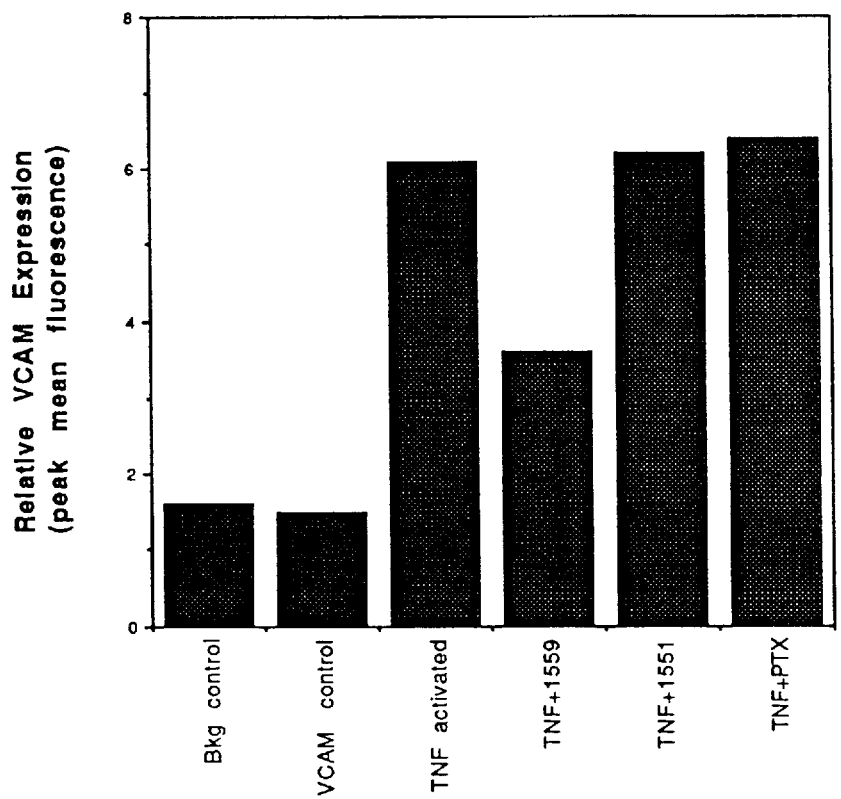
FIG. 6 shows mean fluorescence intensity of cells analyzed by flow cytometry, illustrating the effect of inventive compound no. 1559 on this cell line.

This example illustrates the effect of compound no. 1559 on inhibiting cell surface expression of VCAM in HUVEC cells. The cells were stimulated with TNF-a (20 ng/ml) for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 6 shows an analysis of mean fluorescence intensity of cells analyzed by flow cytometry. The mean fluorescence levels were decreased by compound no. 1559 treatment (1.7 fold decrease) when compared with control levels (TNF treatment, no drug).

EXAMPLE 18

This example illustrates a comparison of MLR (mixed lymphocyte reaction) data for inventive comopounds of varying chain lengths to show a comparison of biological activity as a function of chain length (the number of carbon atoms between the hydroxyl carbon and the core moiety. A mixed lymphocyte reaction was run with a series of inventive compounds and other compounds. IC50 values for each compound tested was determined and the results listed in Table I below:

TABLE I

| Cpnd no | Chain Length | Mean IC50 ($\mu M$) | Formula II | Alcohol type |
|---|---|---|---|---|
| 1551 | 9 | 120 | Y | secondary |
| 1559 | 10 | 150 | Y | primary |
| 1561 | 9 | 185 | Y | diol |
| 1564 | 10 | 210 | Y | diol |
| 1501 | 6 | >500 | N | primary |
| 1502 | 6 | >500 | N | diol |
| 1536 | 8 | 250 | N | secondary |
| 1538 | 8 | >500 | N | diol |
| 1540 | 3 | >500 | N | diol |
| 1542 | 5 | >500 | N | secondary |
| 1545 | 7 | 300 | N | primary |
| 1546 | 8 | 320 | N | primary |
| 1556 | 6 | >500 | N | primary |

Accordingly, these data show the importance of chain length for immune modulating activity in the MLR assay.

EXAMPLE 19

Figure 7A:
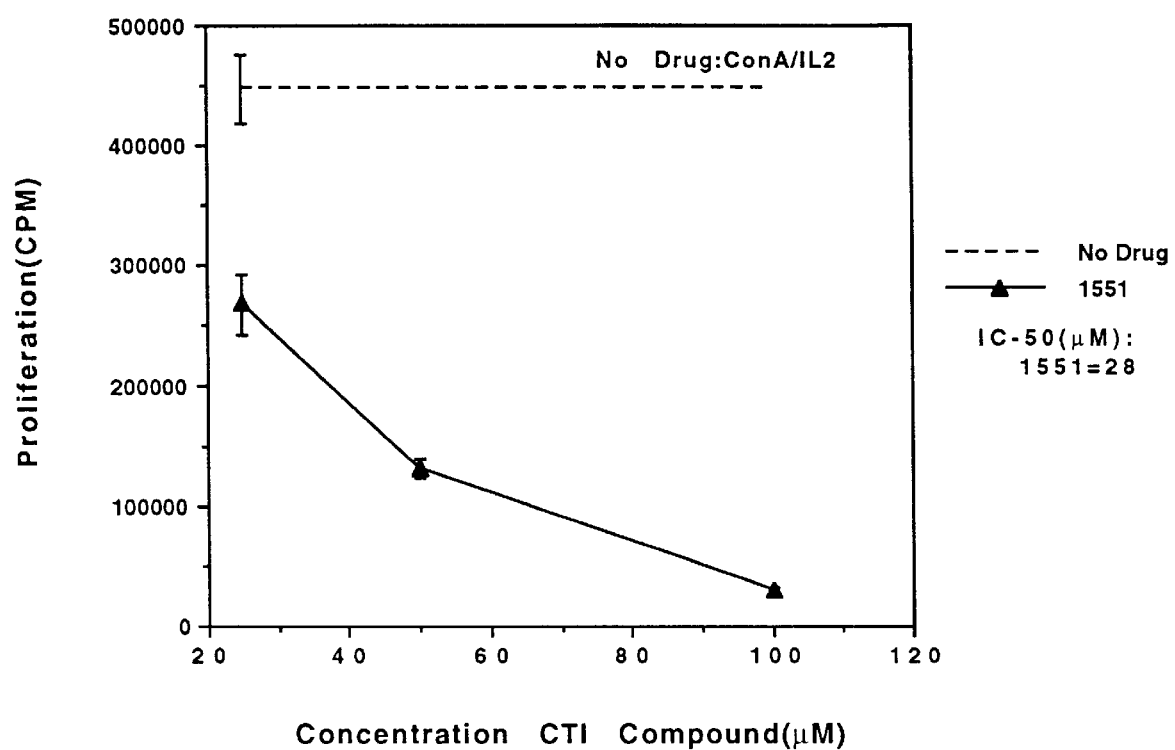
FIGS. 7A and 7B are drug dose response curves for compounds nos. 1551 and 1564 in an assay for murine thymocyte proliferation, co-stimulated by Concanavalin A (ConA) and interleukin-2 alpha (IL-2).
Figure 7B:
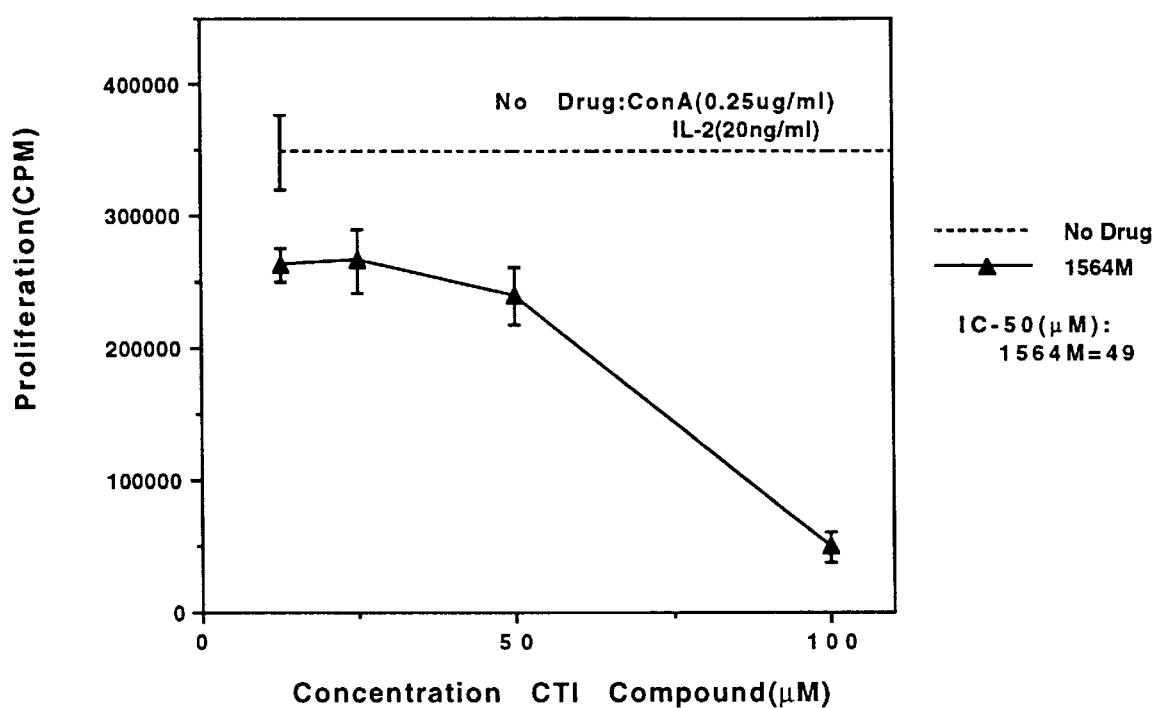

This example illustrates dose response curves used to generate 50% inhibition concentrations (IC50) of inventive compounds nos. 1551 and 1564 for murine thymocyte proliferation, co-stimulated by Concanavalin A (ConA) and interleukin-2 alpha (IL-2). ConA, used to activate CD3, along with IL-2 co-stimulation, induces T-cell proliferation and differentiation. Thymuses, obtained from normal, female Balb/C mice, were dissociated and plated into 96-well plates at a density of $2\times10^5$ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine dye incorporated by the harvested cells was determined in a liquid scintillation counter. Drug doses (shown in FIGS. 7A and 7B) were added two hours prior to ConA and IL-2 activation. Background counts were less than 200 cpm. Both the inventive compounds inhibit thymocyte proliferation and activation and reported IC50 values for compounds nos. 1551 and 1564 are 28 and 49 $\mu M$.

EXAMPLE 19

This example illustrates inhibitive and cytotoxic effects of inventive compounds nos. 2556 and 3504 on Balb/3T3 cell proliferation in response to PDGF-BB stimulation.

Figure 8A:
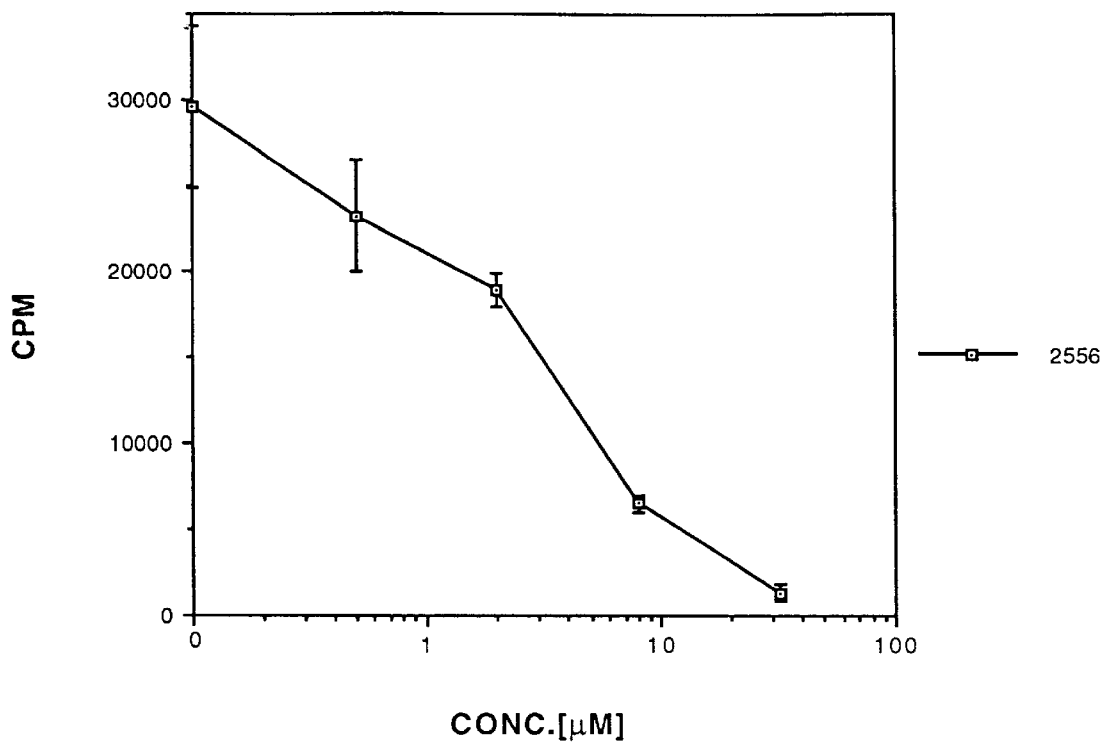
FIGS. 8A and 8B report inhibition activity and cytotoxicity data, respectively, for inventive compound no. 2556 in a Balb/3T3, PDGF-induced proliferation assay.
Figure 8B:
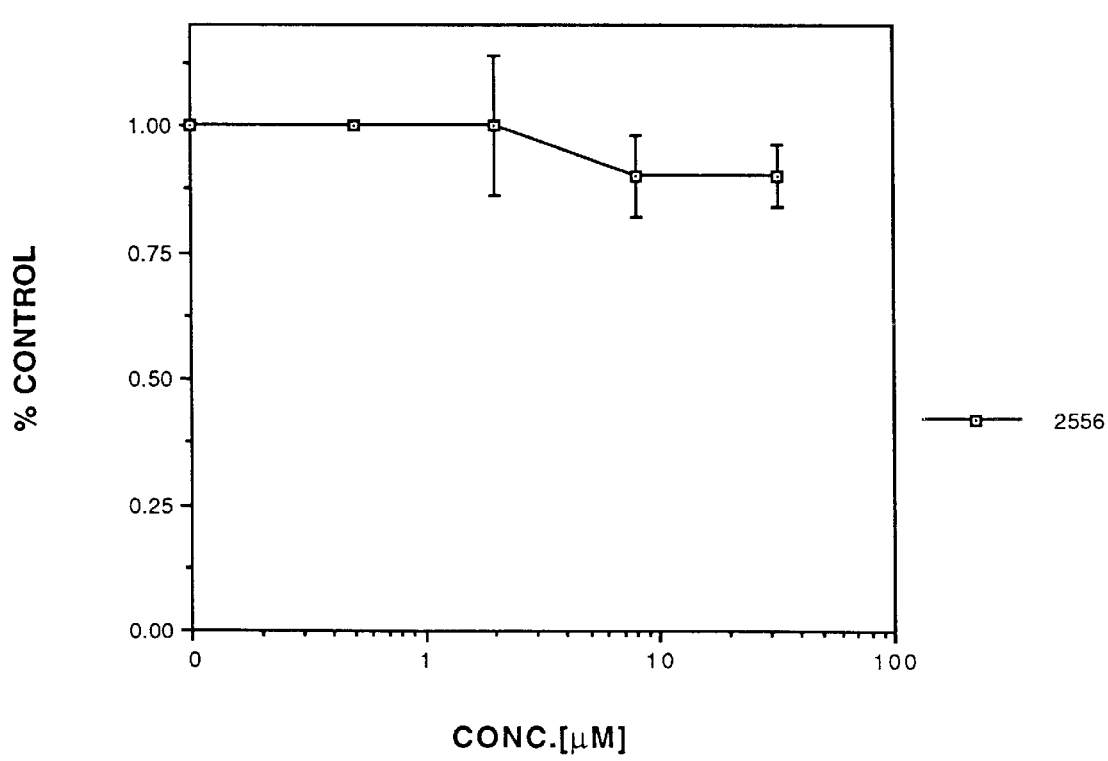
Figure 9A:
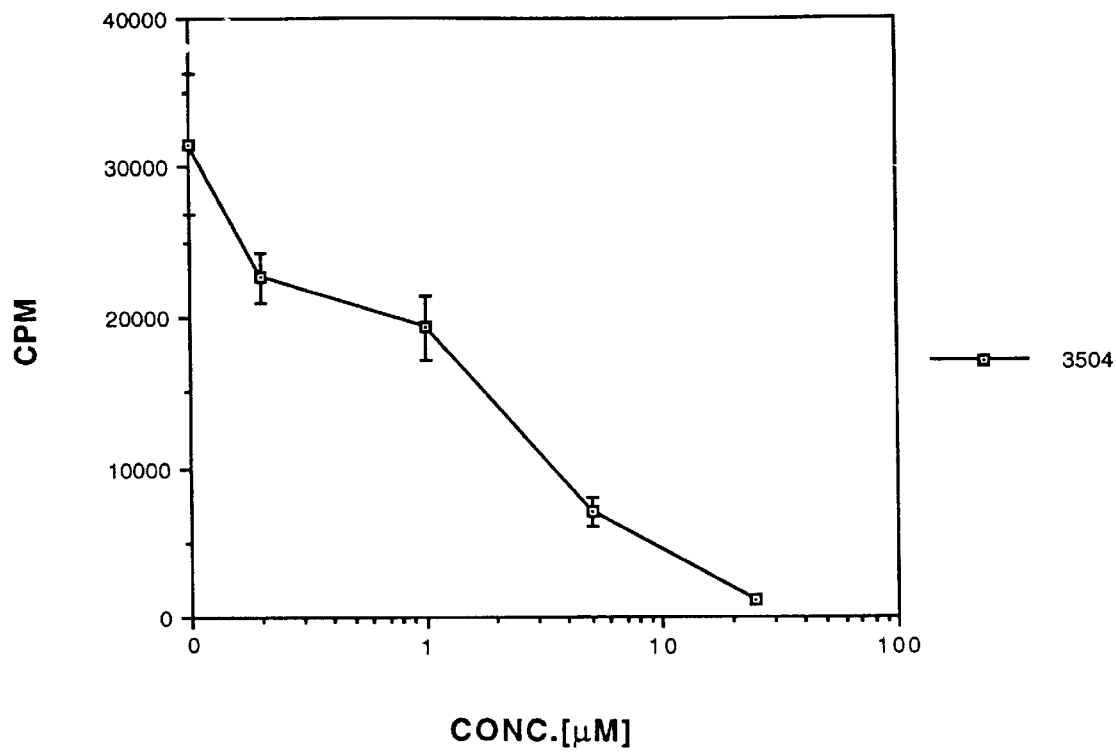
FIGS. 9A and 9B report inhibition activity and cytotoxicity data, respectively, for compounds nos. 2556 and 3504 in a Balb/3T3, PDGF-induced proliferation assay.
Figure 9B:
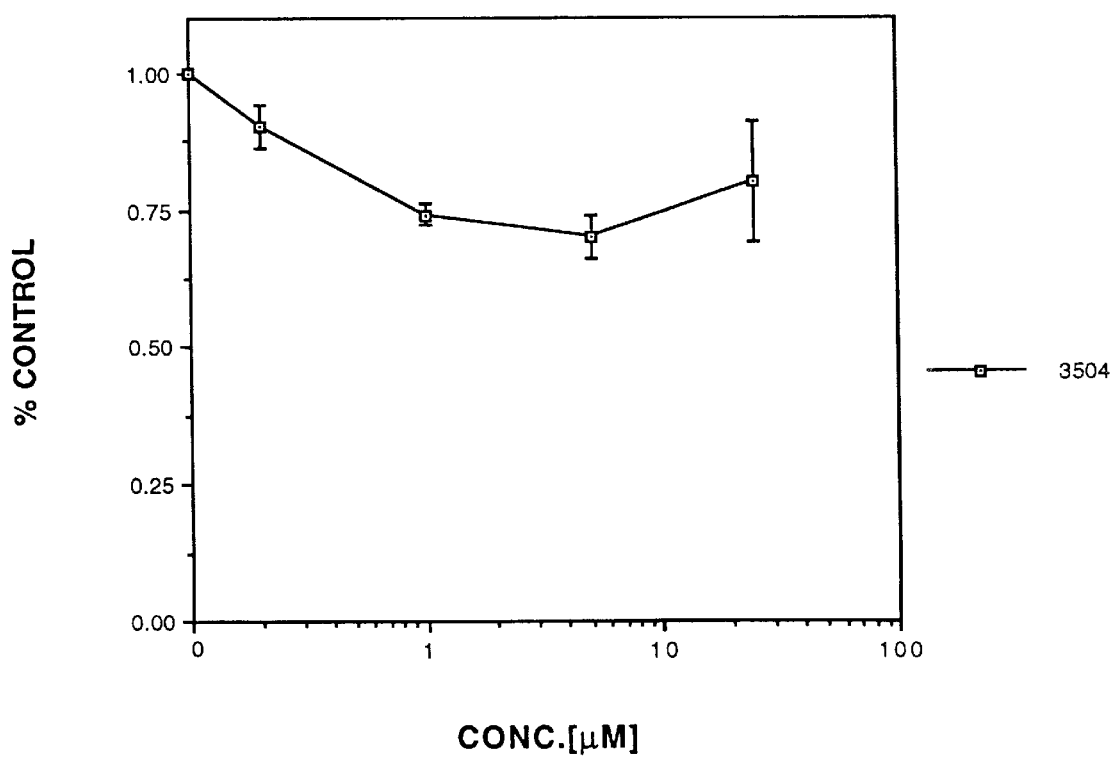

The inventive compounds possess inhibitory effects on PDGF-induced proliferation of Balb/3T3 cells. Balb/3T3 cells respond vigorously to PDGF stimulation, and are useful in vitro models for further study of PDGF-induced proliferation. Disregulated PDGF-proliferative response has been linked to a variety of diseases, including, e.g., restenosis, atherosclerosis, fibrosis, and tumor cell angiogenesis. Cells were plated in low serum-containing medium for 24 hours prior to stimulation with various concentrations (as reported in FIGS. 8A and 9A) of inventive compounds nos.2556 and 3504 (FIGS. 8A and 9A, respectively). PDGF-BB was added at a constant concentration in each assay. Tritiated thymidine was added and cells harvested for scintillation counting 24 hours later. FIGS. 8A and 9A are dose response curves from this assay for compound nos. 2556 and 3504, respectively. FIGS. 8B and 9B report cytotoxicity results for compounds nos. 2556 and 3504 in the Balb/3T3 cell line. Both inventive compounds tested inhibited PDGF-induced proliferation in Balb/3T3 cells.

What is claimed is:

1. A compound, including resolved enantiomers, diastereomers, hydrates, salts, solvates and mixtures thereof, comprising the formula:

(R)j–(core moiety), wherein j is an integer from one to three,
    the core moiety comprises a member selected from the group consisting of substituted or unsubstituted uracilyl, thyminyl and pyrimidinyl,
    R is selected from the group consisting of hydrogen, hydroxyl, amino, substituted or unsubstituted benzyl, $C_{1-6}$alkyl, $C_{1-6}$-alkyl ether, $C_{1-6}$alkenyl and $C_{1-6}$alkenyl ether, wherein at least one R has the formula I:

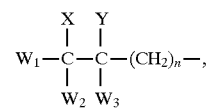

wherein n is an integer from seven to twenty, at least one of X or Y is —OH, another of X or Y, which is not —OH, being selected from the group consisting of hydrogen; $CH_3$—, $CH_3$—$CH_2$—, $CH_3$—$(CH_2)_2$—, $(CH_3)_2$—$CH_2$— and ethers thereof; and each $W_1$, $W_2$, and $W_3$ is independently selected from the group consisting of hydrogen; $CH_3$—, $CH_3$—$CH_2$—, $CH_3$—$(CH_2)_2$—, $(CH_3)_2$—$CH_2$— and ethers thereof; said X, Y, $W_1$, $W_2$, or $W_3$ alkyl groups being unsubstituted or substituted by hydroxyl, halo or dimethylamino.

2. The compound of claim 1, wherein the R $C_{1-6}$alkyl, $C_{1-6}$alkyl ether, $C_{1-6}$alkenyl or $C_{1-6}$alkenyl ether is substituted by a member selected from the group consisting of hydroxyl, halo and dimethylamino.

3. The compound of claim 1, wherein R is selected from the group consisting of hydrogen, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl and 4-chloropentyl.

4. The compound of claim 1, wherein another of X or Y and $W_1$, $W_2$, or $W_3$ are hydrogen or $C_{1-4}$alkyl.

5. The compound of claim 1, wherein n is an integer from seven to twelve.

6. The compound of claim 1, wherein $W_1$, $W_2$, or $W_3$ are independently hydrogen or methyl.

7. The compound of claim 1, wherein the core moiety is selected from the group consisting of alkyl-substituted ($C_{1-6}$) thyminyl; methylthyminyl; alkyl-substituted ($C_{1-6}$) uracilyl; 6-aminouracilyl; 1-methyl-5,6-dihydrouracilyl; 1-methyluracilyl; and 5- and/or 6-position substituted uracilyls.

8. The compound of claim 1, wherein the compound is selected from the group consisting of:

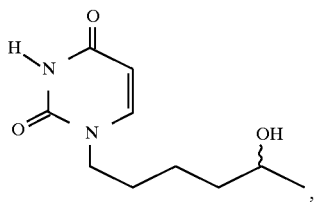

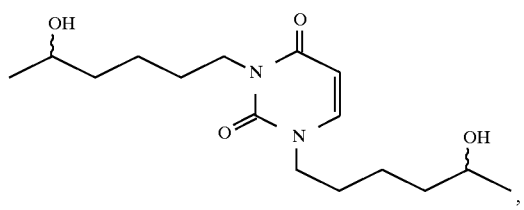

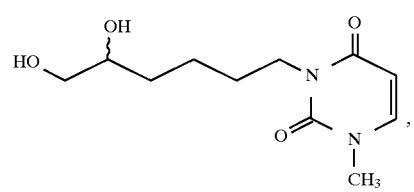

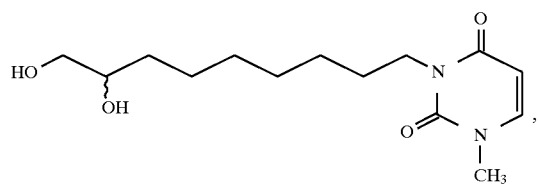

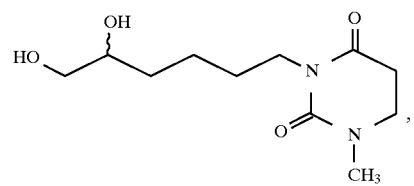

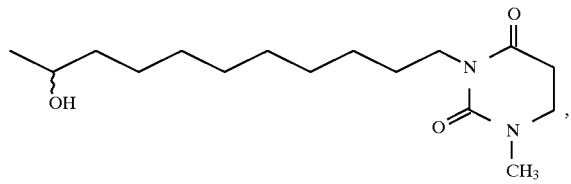

-continued

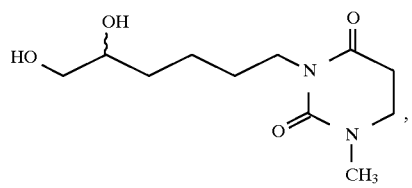

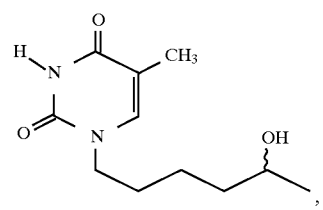

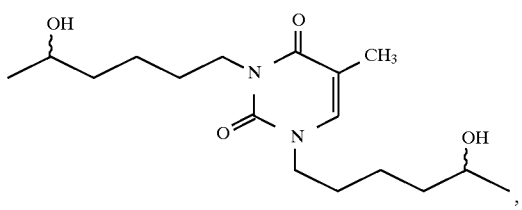

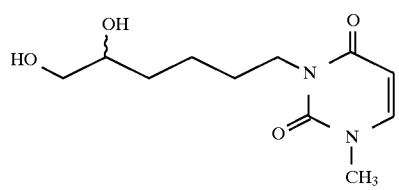

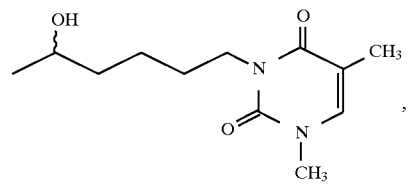

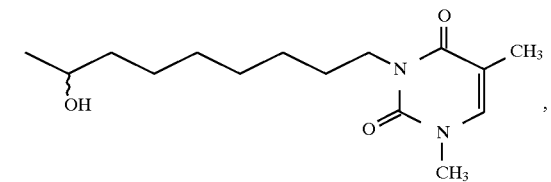

and

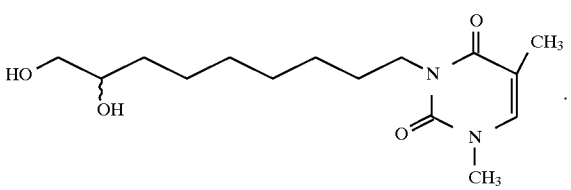

9. A pharmaceutical composition comprising the compound of claim 1 in admixture with a pharmaceutically acceptable excipient or carrier.

* * * * *

UNITED STATES PATENT AND TRADEMARK OFFICE
CERTIFICATE OF CORRECTION

PATENT NO. : 5,804,584
DATED : September 8, 1998
INVENTOR(S) : Underiner et al.

It is certified that error appears in the above-indentified patent and that said Letters Patent is hereby corrected as shown below:

Claim 1, line 45 change "$C_{1-6}$-alkyl ether" to --$C_{1-6}$alkyl ether--.

Signed and Sealed this

First Day of December, 1998

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,804,584

DATED : September 8, 1998

INVENTOR(S) : Underiner, et al.

It is certified that error appears in the above-identified patent and that said Letters Patent is hereby corrected as shown below:

Column 5, line 24, change "FIG. 5 shows" to --Figures 5A, 5B, 5C and 5D show--.

Column 41, line 1, change "FIG. 5 shows" to --Figures 5A, 5B, 5C and 5D show--.

Signed and Sealed this

Twenty-third Day of March, 1999

Attest:

Q. TODD DICKINSON

*Attesting Officer*      *Acting Commissioner of Patents and Trademarks*